(12) United States Patent
Zhang et al.

(10) Patent No.: US 7,383,237 B2
(45) Date of Patent: Jun. 3, 2008

(54) COMPUTER-AIDED IMAGE ANALYSIS

(75) Inventors: Hong Zhang, Savannah, GA (US);
Garry Carls, Tybee Island, GA (US);
Stephen D. Barnhill, Savannah, GA (US)

(73) Assignee: Health Discovery Corporation, Savannah, GA (US)

( * ) Notice: Subject to any disclaimer, the term of this patent is extended or adjusted under 35 U.S.C. 154(b) by 187 days.

(21) Appl. No.: 11/349,542

(22) Filed: Feb. 6, 2006

(65) Prior Publication Data

US 2006/0224539 A1    Oct. 5, 2006

Related U.S. Application Data

(63) Continuation of application No. 10/056,438, filed on Jan. 23, 2002, now Pat. No. 6,996,549, application No. 11/349,542, filed on Feb. 6, 2006, which is a continuation-in-part of application No. 09/633,410, filed on Aug. 7, 2000, now Pat. No. 6,882,990, and a continuation-in-part of application No. 09/578,011, filed on May 24, 2000, now Pat. No. 6,658,395, which is a continuation-in-part of application No. 09/568,301, filed on May 9, 2000, now Pat. No. 6,427,141, which is a continuation of application No. 09/303,387, filed on May 1, 1999, now Pat. No. 6,128,608.

(60) Provisional application No. 60/263,381, filed on Jan. 23, 2001, provisional application No. 60/207,026, filed on May 25, 2000, provisional application No. 60/191,219, filed on Mar. 22, 2000, provisional application No. 60/184,596, filed on Feb. 24, 2000, provisional application No. 60/168,703, filed on Dec. 2, 1999, provisional application No. 60/161,806, filed on Oct. 27, 1999, provisional application No. 60/083,961, filed on May 1, 1998.

(51) Int. Cl.
*G06E 1/00* (2006.01)
*G06E 3/00* (2006.01)
*G06F 15/18* (2006.01)
*G06G 7/00* (2006.01)

(52) U.S. Cl. ....................................................... 706/20
(58) Field of Classification Search ..................... None
See application file for complete search history.

(56) References Cited

U.S. PATENT DOCUMENTS

| | | | |
|---|---|---|---|
| 4,491,627 | A |  | 1/1985 | Iijima et al. |
| 5,235,510 | A |  | 8/1993 | Yamada et al. |
| 5,260,871 | A |  | 11/1993 | Goldberg |
| 5,268,967 | A |  | 12/1993 | Jang et al. |
| 5,289,374 | A |  | 2/1994 | Doi et al. |
| 5,291,560 | A |  | 3/1994 | Daugman |
| 5,331,550 | A |  | 7/1994 | Stafford et al. |
| 5,343,390 | A |  | 8/1994 | Doi et al. |
| 5,359,513 | A |  | 10/1994 | Kano et al. |
| 5,365,429 | A |  | 11/1994 | Carman |
| 5,388,143 | A |  | 2/1995 | MacMahon |
| 5,442,716 | A |  | 8/1995 | Otsu et al. |
| 5,452,367 | A |  | 9/1995 | Bick et al. |
| 5,463,548 | A |  | 10/1995 | Asada et al. |
| 5,475,768 | A |  | 12/1995 | Diep et al. |
| 5,491,627 | A |  | 2/1996 | Zhang et al. |
| 5,537,485 | A |  | 7/1996 | Nishikawa et al. |
| 5,572,565 | A |  | 11/1996 | Abdel-Mottaleb |
| 5,574,799 | A |  | 11/1996 | Bankman et al. |
| 5,579,360 | A |  | 11/1996 | Abdel-Mottaleb |
| 5,586,160 | A |  | 12/1996 | Mascio |
| 5,598,481 | A |  | 1/1997 | Nishikawa et al. |
| 5,615,243 | A |  | 3/1997 | Chang et al. |
| 5,622,171 | A |  | 4/1997 | Asada et al. |
| 5,625,707 | A |  | 4/1997 | Diep et al. |
| 5,625,717 | A |  | 4/1997 | Hashimoto et al. |
| 5,627,907 | A |  | 5/1997 | Gur et al. |
| 5,631,844 | A | * | 5/1997 | Margrey et al. .............. 702/22 |
| 5,633,948 | A |  | 5/1997 | Kegelmeyer, Jr. |
| 5,638,458 | A |  | 6/1997 | Giger et al. |
| 5,657,362 | A |  | 8/1997 | Giger et al. |
| 5,661,820 | A |  | 8/1997 | Kegelmeyer, Jr. |
| 5,666,434 | A |  | 9/1997 | Nishikawa et al. |
| 5,668,888 | A |  | 9/1997 | Doi et al. |
| 5,673,332 | A |  | 9/1997 | Nishikawa et al. |

| | | |
|---|---|---|
| 5,729,620 A | 3/1998 | Wang |
| 5,729,662 A | 3/1998 | Rozmus |
| 5,732,697 A | 3/1998 | Zhang et al. |
| 5,740,266 A | 4/1998 | Weiss et al. |
| 5,740,267 A | 4/1998 | Echerer et al. |
| 5,740,268 A | 4/1998 | Nishikawa et al. |
| 5,757,953 A | 5/1998 | Jang |
| 5,761,334 A | 6/1998 | Nakajima et al. |
| 5,768,333 A | 6/1998 | Abdel-Mottaleb |
| 5,768,406 A | 6/1998 | Abdel-Mottaleb |
| 5,769,074 A | 6/1998 | Barnhill et al. |
| 5,796,862 A | 8/1998 | Pawlicki et al. |
| 5,799,100 A | 8/1998 | Clarke et al. |
| 5,815,591 A | 9/1998 | Roehrig et al. |
| 5,825,910 A | 10/1998 | Vafai |
| 5,825,936 A | 10/1998 | Clarke et al. |
| 5,857,030 A | 1/1999 | Gaborski et al. |
| 5,872,859 A | 2/1999 | Gur et al. |
| 5,917,929 A | 6/1999 | Marshall et al. |
| 5,987,345 A | 11/1999 | Engelmann et al. |
| 5,999,639 A | 12/1999 | Rogers et al. |
| 6,014,452 A | 1/2000 | Zhang et al. |
| 6,018,728 A | 1/2000 | Spence et al. |
| 6,035,056 A | 3/2000 | Karssemeijer |
| 6,055,487 A * | 4/2000 | Margery et al. ............... 702/84 |
| 6,075,879 A | 6/2000 | Roehrig et al. |
| 6,091,841 A | 7/2000 | Rogers et al. |
| 6,115,488 A | 9/2000 | Rogers et al. |
| 6,128,608 A | 10/2000 | Barnhill |
| 6,134,344 A | 10/2000 | Burges |
| 6,137,898 A | 10/2000 | Broussard et al. |
| 6,148,096 A * | 11/2000 | Pressman et al. ........... 382/133 |
| 6,167,146 A | 12/2000 | Rogers et al. |
| 6,192,320 B1 * | 2/2001 | Margrey et al. ............... 702/84 |
| 6,198,838 B1 | 3/2001 | Roehrig et al. |
| 6,205,236 B1 | 3/2001 | Rogers et al. |
| 6,263,092 B1 | 7/2001 | Roehrig et al. |
| 6,266,435 B1 | 7/2001 | Wang |
| 6,301,378 B1 | 10/2001 | Karssemeijer |
| 6,304,675 B1 | 10/2001 | Osbourn et al. |
| 6,317,617 B1 | 11/2001 | Gilhuijs et al. |
| 6,320,976 B1 | 11/2001 | Murthy et al. |
| 6,389,157 B2 | 5/2002 | Rogers et al. |
| 6,404,908 B1 | 6/2002 | Schneider et al. |
| 6,427,141 B1 | 7/2002 | Barnhill |
| 6,434,262 B2 | 8/2002 | Wang |
| 6,442,287 B1 | 8/2002 | Jiang et al. |
| 6,463,438 B1 | 10/2002 | Veltri et al. |
| 6,477,275 B1 | 11/2002 | Melikian et al. |
| 6,535,626 B1 * | 3/2003 | Pressman et al. ........... 382/133 |
| 6,636,634 B2 | 10/2003 | Melikian et al. |
| 6,658,395 B1 | 12/2003 | Barnhill |
| 6,801,645 B1 | 10/2004 | Collins et al. |
| 6,882,990 B1 | 4/2005 | Barnhill et al. |
| 2001/0031076 A1 | 10/2001 | Campanini et al. |
| 2002/0181797 A1 | 12/2002 | Young |
| 2003/0161522 A1 | 8/2003 | Campanini et al. |

FOREIGN PATENT DOCUMENTS

| | | |
|---|---|---|
| EP | 0 663 366 B1 | 7/1995 |
| JP | 03-204783 | 9/1991 |
| JP | 05-101028 | 4/1993 |
| JP | 08-036643 | 2/1996 |

OTHER PUBLICATIONS

Abdolmaleki, "Neural network analysis of breast cancer from MRI findings", *Radiat. Med.*, Sep.-Oct. 1997, pp. 283-293, vol. 15 No. 5, (Abstract).

Adel, "Quality Control of Mammographic Images: Automated Detection of Microcalcifications in Phantom Images", *IWDM 2000, Fifth International Workshop on Digital Mammography*, Jun. 2000, p. 34.

Arana, "Calvarial eosinophilic granutoma: Diagnostic models and image feature selection with a neural network", *Acad. Radiol.* Jun. 1998, pp. 427-434, vol. 5, No. 6 (Abstract).

Barra, "Tissue segmentation on MR images of the brain by possibilistic clustering on a 3D wavelet representation", *J. Magn. Reson. Imaging*, Mar. 2000, pp. 267-278, vol. 11, No. 3 (Abstract).

Bazzani, "Automatic Detection of clustered Micracalcifications in Digital Mammograms using an SVM Classifier", *ESANN'2000 proceedings—European Symposium on Artificial Neural Networks*, XP-002219362, Apr. 26-28, 2000, pp. 195-200, D-Facto public, Bruges, Belgium.

Blot, "Extracting Background Texture in Mammographic Images: A Co-occurence Matrices Based Approach", *IWDM 2000, Fifth International Workshop on Digital Mammography*, Jun. 2000, p. 36.

Bottema, "Detection of Microcalcifications Associated with Cancer", *IWDM 2000, Fifth International Workshop on Digital Mammography*, Jun. 2000, p. 37.

Bruynooghe, M. High Resolution Granulometric Analysis for Early Detection of Small Microcalcification Clusters in X-ray Mammograms, *IWDM 2000, Fifth International Workshop on Digital Mammography*, Jun. 2000, p. 38.

Campanini, "Automatic Detection of Clustered Microcalcifications Using a Combined Method with a Support Vector Machine (SVM) Classifier", *IWDM 2000, Fifth International Workshop on Digital Mammography*, Jun. 2000, p. 39.

Chan, "Computer-aided detection of mammographic microcalcifications: pattern recognition with an artificial neural network", *Med. Phys.*, Oct. 1995, pp. 1555-1567, vol. 22, No. 10 (Abstract).

Chan, Computerized classification of malignant and benign microcalcifications on mammograms, texture analysis using an artificial neural network, *Phys. Med. Biol.*, Mar. 1997, pp. 549-567, vol. 42, No. 3 (Abstract).

Chan, "Computerized analysis of mammographic microcalcifications in morphological and texture feature spaces", *Med. Phys.*, Oct. 1998, pp. 2007-2019, vol. 25, No. 10 (Abstract).

Chang, "Identification of clustered microcalcifications on digitized mammograms using morphology and topography-base computer-aided detection schemes. A preliminary experiment", *Invest. Radiol.* Oct. 1998, pp. 746-751, vol. 33, No. 10, (Abstract).

Dawson, "Nuclear grading of breast carcinoma by image analysis. Classification by multivariate and neural network analysis", *Am. J. Clin. Pathol.*, Apr. 1991, vol. 95,4 Suppl. 1, S29-37, (Abstract).

Decaestecker, "Improving morphology-based malignancy grading schemes in astrocytic tumors by means of computer-assisted techniques", *Brain Pathol.*, Jan. 1998, pp. 29-38, vol. 8, No. 1 (Abstract).

Fields, "Analysis of Computer Extracted Features Related to Size of Micro-Calcifications: Correlation with Pathologic Diagnosis", *IWDM 2000, Fifth International Workshop on Digital Mammography*, Jun. 2000, p. 41.

Floyd, "Case-Based Reasoning Computer Algorithm that Uses Mammographic Findings for Breast Biopsy Decisions", *American Journal of Roentgenology* (2000), XP-002952250, pp. 1347-1352, vol. 175.

Fogel, "Linear and neural models for classifying breast masses", *IEEE Trans. Med. Imaging*, Jun. 1998, pp. 485-488, vol. 17, No. 3 (Abstract).

Freed, "Predictive model for the diagnosis of intraabdominal abscess", *Acad. Radiol.*, Jul. 1998, pp. 473-479, vol. 5, No. 7 (Abstract).

Fukuoka, "Automated Detection and Classification of Masses on Breast Ultrasonograms and its 3D Imaging Technique", *IWDM 2000, Fifth International Workshop on Digital Mammography*, Jun. 2000, p. 42.

Furey, "Support vector machine classification and validation of cancer tissue samples using microarray expression data", *Bioinformatics*, Apr. 4, 2000, pp. 906-914, vol. 16 No. 10 2000, Oxford University Press 2000.

Gavrielides, "Segmentation of suspicious clustered microcalcifications in mammograms", *Med. Phys.*, Jan. 2000, pp. 13-22, vol. 27, No. 1 (Abstract).

Giger, "Computerized Classification of Lesions on Digital Mammography", *IWDM 2000, Fifth International Workshop on Digital Mammography*, Jun. 2000, p. 43.

Golay, "A new correlation-based fuzzy logic clustering algorithm for fMRI", *Magn. Reson. Med.*, Aug. 1998, pp. 249-260, vol. 40, No. 2 (Abstract).

Good, "Detection of Masses and Clustered Microcalcifications on Data Compressed Mammograms", *American Journal of Roentgenology* (2000), pp. 1537-1576, vol. 175.

Hagihara, "Accurate Detection of Microcalcifications on Mammograms by Improvement of Morphological Processing", *IWDM 2000, Fifth International Workshop on Digital Mammography*, Jun. 2000, p. IWDM 2000, Fifth International Workshop on Digital Mammography, Jun. 2000, p. 44.

Hara, "Automated Classification Method of Mammographic Microcalcifications by Using Artificial Neural Network and ACR MI-RADS Criteria of Microcalcification Distribution", *IWDM 2000, Fifth International Workshop on Digital Mammography*, Jun. 2000, p. 45.

Hardin, "Computer-aided diagnosis becomes a reality in mammography", SPIE OE Reports, Jun. 1999, No. 186.

Hatanaka, "An Automatic Detection Algorithm for Masses with a Partial Loss of Region on Mammograms", *IWDM 2000, Fifth International Workshop on Digital Mammography*, Jun. 2000, p. 46.

Heathfield, "Computer-assisted breast cancer grading", *J. Biomed. Eng.*, Oct. 1986, pp. 379-386, vol. 10, No. 5 (Abstract).

Heitman, "Automated detection of spleen volume by spiral CT scans using neural networks and "fuzzy logic"", *Rofo Fortschr. Geb. Rontgenstr. Neuen. Bildgeb Verfahr*, Feb. 2000 pp. 139-146, vol. 172, No. 2 (Abstract).

Henschke, "Neural networks for the analysis of small pulmonary nodules", *Clin. Imaging*, Nov.-Dec. 1997, pp. 390-399, vol. 21, No. 6 (Abstract).

Holmes, "Computer-Aided Diagnosis: An Improved Metric Space for Pixel Signatures", *IWDM, Fifth international Workshop on Digital Mammography*, Jun. 2000, p. 49.

Ishida, "Application of artificial neural networks for quantitative analysis of image data in chest radiographs for detection of interstitial lung disease", *J. Digit Iimaging*, Nov. 1998, pp. 182-192, vol. 11, No. 4 (Abstract).

Huo, "Incorporation of clinical data into a computerized method for the assessment of mammographic breast lesions", *Medical Imaging 2000: Image Processing*, Proc. SPIE , pp. 149-152, vol. 3979 (2000).

Jiang, "Malignant and benign clustered microcalcifications: automated feature analysis and classification", *Radiology*, Mar. 1996, pp. 671-678, vol. 198, No. 3 (Abstract).

Jiang, "Improving breast cancer diagnosis with computer-aided diagnosis", *Acad. Radiol.* Jan. 1999, pp. 22-33, vol. 6, No. 1 (Abstract).

Jiang, "Computer-Aided Diagnosis of Malignant and Benign Microcalcifications in Small-Field Digital Mammograms", *IWDM 2000, Fifth International Workshop on Digital Mammography*, Jun. 2000, p. 51.

Kalman, "Prescreening entire mammograms for masses with artificial neural networks: preliminary results", *Acad. Radiol.*, Jun. 1997, pp. 405-414, vol. 4, No. 6 (Abstract).

Kaufmann, "Automated Detection and Classification of Clustered Microcalcifications Using Morphological Filtering and Statistical Techniques", *IWDM 2000, Fifth International Workshop on Digital Mammography*, Jun. 2000, p. 53.

Kim, "Statistical textural features for detection of microcalcifications in digitized mammograms", *IEEE Trans. Med. Imaging*, Mar. 1999, pp. 231-238, vol. 18, No. 3 (Abstract).

Kopans, "Double reading", *Radiol. Clin. North Am.*, Jul. 2000, vol. 38, No. 4, pp. 719-724, (Abstract).

Kovalerchuk, "Fuzzy logic in computer-aided breast cancer diagnosis: analysis of lobulation", *Artif. Intell. Med.*, Sep. 1997, pp. 75-85, vol. 11, No. 1 (Abstract).

Lau, "automated detection of breast tumors using the asymmetry approach", *Comput. Biomed. Res.*, Jun. 1991, pp. 273-295, vol. 24, No. 3 (Abstract).

Leavers, "Use of the Two-dimensional Radon Transform to Generate a Taxonomy of Shape for the Characterization of Abrasive Powder Particles", *IEEE Transactions on Pattern Analysis and Machine Intelligence*, Dec. 2000, pp. 1411-1423, vol. 22, No. 12.

Lee, "Classification of Masses in Screening Mammograms as Benign or Malignant", *IWDM 2000, Fifth International Workshop on Digital Mammography*, Jun. 2000, p. 54.

Lo, "Evolutionary programming technique for reducing complexity of artificial neural networks for breast cancer diagnosis", *Medical Inaging 2000 Image Processing*, Proc. SPIE, 2000, pp. 153-158 vol. 3979.

Lu, "Classifying Lobular and DCIS Microcalcifications", *IWDM 2000, Fifth International Workshop on Digital Mammography*, Jun. 2000, p. 56.

Madsen, "Pulmonary CT image classification with evolutionary programming", *Acad. Radiol.*, Dec. 1999, pp. 736-741, vol. 6, No. 12 (Abstract).

Mudigonda, "Segmentation and classification of mammographic masses", *Medical Imaging 2000: Image Processing*, Proc. SPIE, Feb. 2000; pp. 55-67, vol. 3979.

Ngan, "Analysis of functional magnetic resonance imaging data using self-organizing mapping with spatial connectivity", *Magn. Reson. Med.*, May 1999, pp. 939-946, vol. 41, No. 5 (Abstract).

O'Leary, "Computer-assisted image interpretation: use of a neural network to differentiate tubular carcinoma from sclerosing adenosis", *Mod. Pathol.*, Jul. 1992, pp. 402-405, vol. 5, No. 4 (Abstract).

Pantazopoulos, "Back propagation neural network in the discrimination of benign from malignant lower urinary tract lesions", *J. Urol.*, May 1998, pp. 1619-1623,vol. 159, No. 5 (Abstract).

Patrick, "Expert learning system network for diagnosis of breast calcifications", *Invest. Radiol.* , Jun. 1991, pp. 534-539, vol. 26, No. 6 (Abstract).

Pavlopoulos, "Fuzzy neural network-based texture analysis of ultrasonic images", *IEEE Eng. Med. Biol. Mag.*, Jan.-Feb. 2000, pp. 39-47, vol. 19, No. 1 (Abstract).

Petrick, "Preclinical Evaluation of a CAD Algorithm for Early Detection of Breast Cancer", *IWDM 2000, Fifth International Workshop on Digital Mammography*, Jun. 2000, p. 63.

Qian, "Digital mammography: comparison of adaptive and nonadaptive CAD methods for mass detection", *Acad. Radiol.*, Aug. 1999, pp. 471-480, vol. 6, No. 8 (Abstract).

Racz, "Computer Aided Diagnosis Based on Analysis of Microcalcifications", *IWDM 2000, Fifth International Workshop on Digital Mammography*, Jun. 2000, p. 67.

Sahiner, "Active Contour Models for Segmentation and Characterization of Mammographic Masses", *IWDM 2000, Fifth International Workshop on Digital Mammography*, Jun. 2000, p. 68.

Scott, "Using artificial neural network analysis of global ventilation-perfusion scan morphometry as a diagnistic tool", *AJR Am. J. Roentgenol.*, Oct. 1999, pp. 943-948, vol. 173, No. 4 (Abstract).

Sendra, "Methodology of Interactive Segmentation and Feature Analysis of Masses in Digitized Mammograms", *IWDM 2000, Fifth International Workshop on Digital Mammography*, Jun. 2000, p. 70.

Sivaramakrishna, "Comparing the Performance of Mammographic Enhancement Algorithms", *Americal Journal of Roentgenology* (2000), pp. 45-51, vol. 175.

Valverde, "Elimination of Calcified False Positives in Detection of Microcalcifications in Mammograms Using Hough Transform", *IWDM 2000, Fifth International Workshop on Digital Mammography*, Jun. 2000, p. 72.

Van Tonder, "The patch work engine: image segmentation from shape symmetries", *Neural. Netw.*, Apr. 2000, pp. 291-303, vol. 13, No. 3 (Abstract).

Veldkamp, "Fully Automated Classification of Microcalcification Cases Referred from a Nation-Wide Screening Program", *IWDM 2000, Fifth International Workshop on Digital Mammography*, Jun. 2000, p. 73.

Velthuizen, "Feature extraction for MRI segmentation", *J. Neuroimaging*, Apr. 1999, pp. 85-90, vol. 9, No. 2 (Abstract).

Velthuizen, "Computer Description of Mammographic Masses", *IWDM 2000, Fifth International Workshop on Digital Mammography*, Jun. 2000, p. 74.

Velthuizen, "Mammographic mass classification: Initial results", *Medical Imaging 2000: Image Processing*, Proc. SPIE, 2000, pp. 68-76, vol. 3979.

Wolberg, "Image analysis and machine learning applied to breast cancer diagnosis and prognosis", *Anal. Quant. Cytol. Histol.*, Apr. 1995, pp. 77-87, vol. 17, No. 2 (Abstract).

Woo, "Evaluation of the Architecture Similarity Between Left and Right Breast", *IWDM 2000, Fifth International Workshop on Digital Mammography*, Jun. 2000, p. 75.

Wu, "Detection of lung nodules in digital chest radiographsusing artificial neural networks: a pilot study", *J. Digit. Imaging*, May 1995, pp. 88-94, vol. 8, No. 2, (Abstract).

Wu, "Computerized detection of clustered microcalcifications in digital mammograms: applications of artificial neural networks", *Med. Phys.*, May-Jun. 1992, pp. 555-560, vol. 19, No. 3, (Abstract).

Wu, "artificial neural networks in mammography: application to decision making in the diagnosis of breast cancer", *Radiology*, Apr. 1993, pp. 81-87, vol. 187, No. 1, (Abstract).

Yoshida, "An Improved computer-assisted disgnostic scheme using wavelet transform for detecting clustered microcalcifications in digital mammograms", *Acad. Radiol.*, Aug. 1996, pp. 621-627, vol. 3, No. 8, (Abstract).

Zhang, "Computerized detection of clustered microcalcifications in digital mammograms using a shift-invariant artificial neural network", *Med. Phys.*, Apr. 1994, , pp. 517-524, vol. 21, No. 4 (Abstract).

Zhang, "An improved shift-invariant artificial neural network for computerized detection of clustered microcalcificationsin digital mammograms", *Med. Phys.*, Apr. 1996, pp. 595-601, vol. 23, No. 4 (Abstract).

Zhou, "Computerized image analysis: Estimation of breast density on mammograms", *medical imaging 2000: Image Processing*, Proc. SPIE , 2000), pp. 1615-1624, vol. 3979.

Arodz, et al., "A 3D Visualization System for Computer-Aided Mammogram Analysis", *DTC Research Report 2004/20*, Aug. 2004, pp. 1-19, vol. 1-19, vol. 20, Digital technology Center, University of Minnesota.

Arodz, et al., "Detection of Clustered Microcalcifications in Small Field Digital Mammography", *Computer Methods and Programs in Biomedicine*, Jan. 2006, pp. 56-65, vol. 81(1).

Campanini, et al., "A novel featureless approach to mass detection in digital mammograms based on Support Vector Machines", *Physics in Medicine and Biology*, Mar. 2004, pp. 961-976, vol. 49, No. 6.

El-Naqa, et al., "Support vector machine learning for detection of microcalcifications in mammograms", *Proceedings—IEEE Symposium on Biomedical Imaging*, 2002, pp. 201-204.

El-Naqa, et al., "A Support Vector Machine Learning Approach for Detection Of Microcalcifications", *IEEE Transactions on Medical Imaging*, Dec. 2002, pp. 1552-1563, vol. 21, No. 12.

Fu, et al., "Image segmentation feature selection and pattern classification for mammographic microcalcifications", *Computerized Medical Imaging and Graphics*, 2005, p. 419-429, vol. 29.

Masotti, M., "Exploring ranklets performances in mammographic mass classification using recursive feature elimination", *IEEE International Conference on Image Processing*, Sep. 2005, pp. 1-4, Genova, Italy.

Yuen, et al., "An integrated Approach to Mammogram Analysis", *A Poster*, 2005, Digital Technology Center, University of Minnesota, Minneapolis, Minnesota.

Urahama, Kiichi & Hidaka, Kyosuke, "Group model of dot pattern by non-linear gravity", *IEICE Transactions*, Nov. 8, 1994, vol. 94, No. 294, pp. 75-82.

\* cited by examiner

*Primary Examiner*—Michael B Holmes
(74) *Attorney, Agent, or Firm*—Procopio, Cory, Hargreaves & Savitch LLP

(57) ABSTRACT

Digitized image data are input into a processor where a detection component identifies the areas (objects) of particular interest in the image and, by segmentation, separates those objects from the background. A feature extraction component formulates numerical values relevant to the classification task from the segmented objects. Results of the preceding analysis steps are input into a trained learning machine classifier which produces an output which may consist of an index discriminating between two possible diagnoses, or some other output in the desired output format. In one embodiment, digitized image data are input into a plurality of subsystems, each subsystem having one or more support vector machines. Pre-processing may include the use of known transformations which facilitate extraction of the useful data. Each subsystem analyzes the data relevant to a different feature or characteristic found within the image. Once each subsystem completes its analysis and classification, the output for all subsystems is input into an overall support vector machine analyzer which combines the data to make a diagnosis, decision or other action which utilizes the knowledge obtained from the image.

20 Claims, 12 Drawing Sheets

| 406a | 406b | 406c | 406d | 406e | 406f |
|---|---|---|---|---|---|
| 41 | 75 | 95 | 29 | 8 | 1 |
| 47 | 64 | 45 | 26 | 4 | 1 |
| 34 | 35 | 17 | 11 | 5 | 1 |
| 48 | 5 | 137 | 18 | 2 | 1 |
| 35 | 29 | 48 | 21 | 9 | 1 |
| 49 | 19 | 69 | 11 | 7 | 1 |
| 42 | 8 | 10 | 12 | 2 | 1 |
| 44 | 3 | 12 | 14 | 1 | 1 |
| 37 | 57 | 19 | 20 | 7 | 1 |
| 48 | 17 | 14 | 12 | 1 | 1 |
| 39 | 1 | 10 | 17 | 8 | 1 |
| 44 | 21 | 14 | 17 | 1 | 1 |
| 34 | 2 | 9 | 12 | 1 | 1 |
| 31 | 10 | 10 | 16 | 0 | 1 |
| 42 | 252 | 452 | 25 | 0 | 1 |
| 42 | 59 | 693 | 19 | 1 | -1 |
| 36 | 5 | 51 | 12 | 1 | -1 |
| 38 | 1 | 10 | 19 | 1 | -1 |
| 36 | 43 | 89 | 9 | 1 | -1 |
| 42 | 16 | 10 | 13 | 4 | -1 |
| 47 | 19 | 20 | 12 | 1 | -1 |
| 49 | 14 | 128 | 21 | 4 | -1 |
| 38 | 169 | 315 | 36 | 0 | -1 |
| 33 | 2 | 12 | 8 | 0 | -1 |
| 46 | 41 | 308 | 23 | 5 | -1 |
| 44 | 54 | 115 | 29 | 2 | -1 |
| 31 | 4 | 3 | 20 | 1 | -1 |
| 49 | 1 | 18 | 27 | 2 | -1 |
| 48 | 34 | 355 | 19 | 3 | -1 |
| 44 | 29 | 19 | 20 | 2 | -1 |
| 42 | 207 | 11 | 10 | 3 | -1 |
| 43 | 62 | 53 | 26 | 1 | -1 |
| 43 | 108 | 293 | 4 | 0 | -1 |
| 35 | 25 | 13 | 24 | 1 | -1 |
| 35 | 5 | 5 | 16 | 1 | -1 |
| 45 | 54 | 17 | 19 | 8 | -1 |
| 41 | 4 | 10 | 15 | 4 | -1 |
| 40 | 8 | 12 | 8 | 0 | -1 |
| 42 | 25 | 78 | 21 | 2 | -1 |
| 46 | 30 | 105 | 11 | 5 | -1 |
| 48 | 72 | 94 | 15 | 1 | -1 |
| 36 | 3 | 10 | 7 | 0 | -1 |
| 46 | 165 | 12 | 17 | 5 | -1 |
| 47 | 22 | 10 | 26 | 2 | -1 |
| 48 | 3 | 10 | 21 | 0 | -1 |
| 40 | 4 | 10 | 12 | 0 | -1 |
| 32 | 3 | 10 | 14 | 6 | 1 |
| 36 | 51 | 167 | 11 | 3 | 1 |
| 39 | 4 | 15 | 31 | 25 | 1 |
| 46 | 2 | 10 | 8 | 0 | 1 |
| 28 | 12 | 36 | 25 | 23 | 1 |
| 32 | 23 | 50 | 19 | 0 | 1 |
| 44 | 26 | 10 | 21 | 4 | 1 |
| 47 | 32 | 11 | 21 | 7 | 1 |
| 42 | 32 | 41 | 21 | 18 | -1 |
| 42 | 2 | 10 | 14 | 0 | -1 |
| 36 | 10 | 1 | 16 | 1 | -1 |
| 47 | 5 | 6 | 22 | 1 | -1 |
| 34 | 18 | 6 | 13 | 2 | -1 |
| 34 | 9 | 10 | 29 | 0 | -1 |
| 37 | 6 | 10 | 16 | 0 | -1 |
| 38 | 42 | 46 | 14 | 6 | -1 |
| 32 | 98 | 11 | 11 | 0 | -1 |
| 37 | 39 | 10 | 13 | 1 | -1 |
| 45 | 17 | 267 | 20 | 4 | -1 |
| 39 | 93 | 134 | 12 | 1 | -1 |
| 43 | 47 | 11 | 19 | 11 | -1 |
| 46 | 6 | 10 | 13 | 1 | -1 |
| 49 | 1 | 4 | 19 | 6 | -1 |
| 46 | 172 | 302 | 9 | 3 | -1 |

402 (upper group), 404 (lower group)

FIG.4

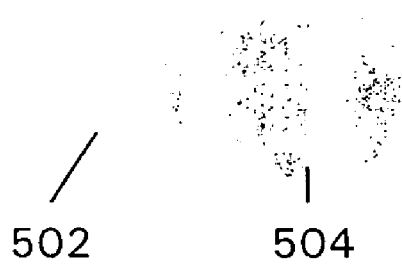 
FIG. 5a                    FIG. 5b

FIG.6

COMPUTER-AIDED IMAGE ANALYSIS

RELATED APPLICATIONS

This application is a continuation of application Ser. No. 10/056,438, filed Jan. 23, 2002, issued Feb. 7, 2006 as Pat. No. 6,996,549, which claims the benefit of priority of U.S. provisional application Ser. No. 60/263,381 filed Jan. 23, 2001. This application is also a continuation-in-part of application Ser. No. 09/633,410, filed Aug. 7, 2000, now issued as Pat. No. 6,882,990, which claims priority to provisional applications No. 60/161,806, filed Oct. 27, 1999, No. 60/168,703, filed Dec. 2, 1999, No. 60/184,596, filed Feb. 24, 2000, No. 60/191,219 filed Mar. 22, 2000 and No. 60/207,026, filed May 25, 2000, and is a continuation-in-part of application Ser. No. 09/578,011, filed May 24, 2000, now issued as Pat. No. 6,658,395, which is a continuation-in-part of application Ser. No. 09/568,301, filed May 9, 2000, now issued as U.S. Pat. No. 6,427,141, which is a continuation of application Ser. No. 09/303,387, filed May 1, 1999, now issued as U.S. Pat. No. 6,128,608, which claims priority to U.S. provisional application Ser. No. 60/083,961, filed May 1, 1998. This application is related to co-pending applications Ser. No. 09/633,615, now abandoned, Ser. No. 09/633,616, now issued as Pat. No. 6,760,715, and Ser. No. 09/633,850, now issued as Pat. No. 6,789,069, all filed Aug. 7, 2000 which are also continuations-in-part of application Ser. No. 09/578,011. This application is also related to applications Ser. No. 09/303,386, now abandoned, and Ser. No. 09/305,345, now issued as U.S. Pat. No. 6,157,921, both filed May 1, 1999, and to application Ser. No. 09/715,832, filed Nov. 14, 2000, now abandoned, all of which also claim priority to provisional application Ser. No. 60/083,961.

FIELD OF THE INVENTION

The present invention relates generally to computer-aided analysis of images and more particularly to computer-aided image analysis using support vector machines.

BACKGROUND OF THE INVENTION

Optimal extraction of data contained within an electromagnetic signal requires the ability to identify important components of the signal in spite of noise and limitations of the signal source and the instrumentation used to detect the signal. A key area in which optimized extraction and reconstruction of data is sought is the field of image analysis, where sources of noise and other factors can negatively impact the ability to efficiently extract data from the image, thus impairing the effectiveness of the imaging method for its intended use. Examples of areas in which image analysis can be problematic include astronomical observation and planetary exploration, where sources can be faint and atmospheric interference introduce noise and distortion, military and security surveillance, where light can be low and rapid movement of targets result in low contrast and blur, and medical imaging, which often suffers from low contrast, blur and distortion due to source and instrument limitations. Adding to the difficulty of image analysis is the large volume of data contained within a digitized image, since the value of any given data point often cannot be established until the entire image is processed.

Development of methods for automated analysis of digital images has received considerable attention over that past few decades, with one of the key areas of interest being the medical field. Applications include analysis of pathology images generated using visual, ultrasound, x-ray, positron emission, magnetic resonance and other imaging methods. As in the case of human-interpreted medical images, an automated image analyzer must be capable of recognizing and classifying blurred features within the images, which often requires discrimination of faint boundaries between areas differing by only a few gray levels or shades of color.

In recent years, machine-learning approaches for image analysis have been widely explored for recognizing patterns which, in turn, allow extraction of significant features within an image from a background of irrelevant detail. Learning machines comprise algorithms that may be trained to generalize using data with known outcomes. Trained learning machine algorithms may then be applied to predict the outcome in cases of unknown outcome. Machine-learning approaches, which include neural networks, hidden Markov models, belief networks and support vector machines, are ideally suited for domains characterized by the existence of large amounts of data, noisy patterns and the absence of general theories. Particular focus among such approaches has been on the application of artificial neural networks to biomedical image analysis, with results reported in the use of neural networks for analyzing visual images of cytology specimens and mammograms for the diagnosis of breast cancer, classification of retinal images of diabetics, karyotyping (visual analysis of chromosome images) for identifying genetic abnormalities, and tumor detection in ultrasound images, among others.

The majority of learning machines that have been applied to image analysis are neural networks trained using back-propagation, a gradient-based method in which errors in classification of training data are propagated backwards through the network to adjust the bias weights of the network elements until the mean squared error is minimized. A significant drawback of back-propagation neural networks is that the empirical risk function may have many local minimums, a case that can easily obscure the optimal solution from discovery. Standard optimization procedures employed by back-propagation neural networks may converge to a minimum, but the neural network method cannot guarantee that even a localized minimum is attained, much less the desired global minimum. The quality of the solution obtained from a neural network depends on many factors. In particular, the skill of the practitioner implementing the neural network determines the ultimate benefit, but even factors as seemingly benign as the random selection of initial weights can lead to poor results. Furthermore, the convergence of the gradient-based method used in neural network learning is inherently slow. A further drawback is that the sigmoid function has a scaling factor, which affects the quality of approximation. Possibly the largest limiting factor of neural networks as related to knowledge discovery is the "curse of dimensionality" associated with the disproportionate growth in required computational time and power for each additional feature or dimension in the training data.

The shortcomings of neural networks can be overcome by using another type of learning machine—the support vector machine. In general terms, a support vector machine maps input vectors into high dimensional feature space through a non-linear mapping function, chosen a priori. In this high dimensional feature space, an optimal separating hyperplane is constructed. The optimal hyperplane is then used to determine perform operations such as class separations, regression fit, or density estimation.

Within a support vector machine, the dimensionally of the feature space may be very high. For example, a fourth degree polynomial mapping function causes a 200 dimensional input space to be mapped into a 1.6 billion dimensional feature space. The kernel trick and the Vapnik-Chervonenkis ("VC") dimension allow the support vector machine to avoid the "curse of dimensionality" that typically limits other methods and effectively derive generalizable answers from this very high dimensional feature space.

If the training vectors are separated by the optimal hyperplane (or generalized optimal hyperplane), the expected value of the probability of committing an error on a test example is bounded by the examples in the training set. This bound depends on neither the dimensionality of the feature space, the norm of the vector of coefficients, nor the bound of the number of the input vectors. Therefore, if the optimal hyperplane can be constructed from a small number of support vectors relative to the training set size, the generalization ability will be high, even in infinite dimensional space.

As such, support vector machines provide a desirable solution for the problem of analyzing a digital image from vast amounts of input data. However, the ability of a support vector machine to analyze a digitized image from a data set is limited in proportion to the information included within the training data set. Accordingly, there exists a need for a system and method for pre-processing data so as to augment the training data to maximize the computer analysis of an image by the support vector machine.

BRIEF SUMMARY OF THE INVENTION

The system and method for analyzing digitized images uses a learning machine in general and a support vector machine in particular. A training data set consisting of digital image data generated from imaging a biological or medical subject with known outcome is pre-processed to allow the most advantageous application of the learning machine. For purposes of the present invention, the image can be derived ex vivo, e.g., a tissue sample viewed through a microscope, or in vivo, e.g., an x-ray projection image. Each training data point comprises a vector having one or more coordinates. Pre-processing the training data set comprises identifying missing or erroneous data points and taking appropriate steps to correct the flawed data or, as appropriate, remove the observation or the entire field from the scope of the problem. Pre-processing the training data set may also comprise adding dimensionality to each training data point by adding one or more new coordinates to the vector. The new coordinates added to the vector may be derived by applying a transformation to one or more of the original coordinates. The transformation may be based on expert knowledge, or may be computationally derived. In a situation where the training data set comprises a continuous variable, the transformation may comprise optimally categorizing the continuous variable of the training data set.

The support vector machine is trained using the pre-processed training data set. In this manner, the additional representations of the training data provided by the preprocessing enhances the learning machine's ability to analyze the data therefrom. In the particular context of support vector machines, the greater the dimensionality of the training set, the higher the quality of the generalizations that may be derived therefrom. When the analysis to be performed from the data relates to a regression or density estimation or where the training output comprises a continuous variable, the training output may be post-processed by optimally categorizing the training output to derive categorizations from the continuous variable.

A test data set is pre-processed in the same manner as was the training data set: Then, the trained learning machine is tested using the pre-processed test data set. A test output of the trained learning machine may be post-processed to determine if the test output is an optimal solution. Post-processing the test output may comprise interpreting the test output into a format that may be compared with the test data set. Alternative post-processing steps may enhance the human interpretability or suitability for additional processing of the output data.

In the context of a support vector machine, a method is provided for the selection of a kernel prior to training the support vector machine. The selection of a kernel may be based on prior knowledge of the specific problem being addressed or analysis of the properties of any available data to be used with the learning machine and is typically dependant on the nature of the analysis to be made from the data. Optionally, an iterative process comparing post-processed training outputs or test outputs can be applied to make a determination as to which configuration provides the optimal solution. If the test output is not the optimal solution, the selection of the kernel may be adjusted and the support vector machine may be retrained and retested. When it is determined that the optimal solution has been identified, a live data set, i.e., a data set with unknown results, may be collected and pre-processed in the same manner as was the training data set. The pre-processed live data set is input into the learning machine for processing. The live output of the learning machine may then be post-processed by interpreting the live output into a computationally derived alphanumeric classifier.

In an exemplary embodiment, a system is provided for analysis of a digitized image from image data using a support vector machine. The exemplary system comprises a storage device for storing a database containing a training data set and a test data set, each data set comprising image data, and a processor for executing one or more support vector machines. The processor is also operable for collecting the training data set from the database, pre-processing the training data set to enhance each of a plurality of training data points, training the support vector machine using the pre-processed training data set, collecting the test data set from the database, pre-processing the test data set in the same manner as was the training data set, testing the trained support vector machine using the pre-processed test data set, and in response to receiving the test output of the trained support vector machine, post-processing the test output to determine if the test output is an optimal solution. The exemplary system may also comprise a communications device for receiving the test data set and the training data set from a remote source. In such a case, the processor may be operable to store the training data set in the storage device prior to pre-processing of the training data set and to store the test data set in the storage device prior to pre-processing of the test data set. The exemplary system may also comprise a display device for displaying the post-processed test data. The processor of the exemplary system may further be operable for performing each additional function described above. The communications device may be further operable to send a computationally-derived alphanumeric classifier to a remote source.

In an exemplary image analysis sequence using kernel-based learning machines, in particular, support vector machines, digitized image data are input into the processor where a detection component identifies the areas (objects) of particular interest in the image and, by segmentation, separates those objects from the background. A feature extraction component formulates numerical values relevant to the classification task from the segmented objects. Results of the preceding analysis steps are input into a support vector machine classifier which produces an output which may consist of an index discriminating between two possible diagnoses, or some other output in the desired output format. Additional support vector machines may be included to assist in the segmentation or feature extraction components prior.

In a preferred embodiment, digitized image data are input into a plurality of subsystems, each subsystem having one or more kernel-based learning machine. Each subsystem analyzes the data relevant to a different feature or characteristic found within the image. For example, using the example of mammogram analysis, one subsystem may look at and classify calcifications, another subsystem may look at and classify masses, while a third subsystem looks at and classifies structural distortions. Once each subsystem completes its analysis and classification, the output for all subsystems is input into an overall kernel-based, e.g., support vector machine, analyzer which combines the data to make a diagnosis, decision or other action which utilizes the knowledge obtained from the image.

Specific procedures for the preprocessing of data and training of support vector machines is described in U.S. Pat. Nos. 6,157,921 and 6,128,608 which are incorporated herein by reference in their entirety. For processing of image data, pre-processing may include the use of known transformations which facilitate extraction of the useful data. Such transformations may include, but are not limited to, Fourier transforms, wavelet transforms, Radon transforms and Hough transforms.

BRIEF DESCRIPTION OF THE DRAWINGS

Exemplary embodiments of the present invention will hereinafter be described with reference to the below-listed drawings, in which like numerals indicate like elements throughout the figures.

FIG. 4 illustrates an exemplary unexpanded data set that may be input into a support vector machine.

FIGS. 5a and 5b are diagrams of gray scale features in an image, where FIG. 5a illustrates the un-processed image and FIG. 5b illustrates the image after segmentation pre-processing.

FIG. 6 illustrates an exemplary expanded data set that may be input into a support vector machine.

DETAILED DESCRIPTION OF THE PREFERRED EMBODIMENTS

Figure 1:
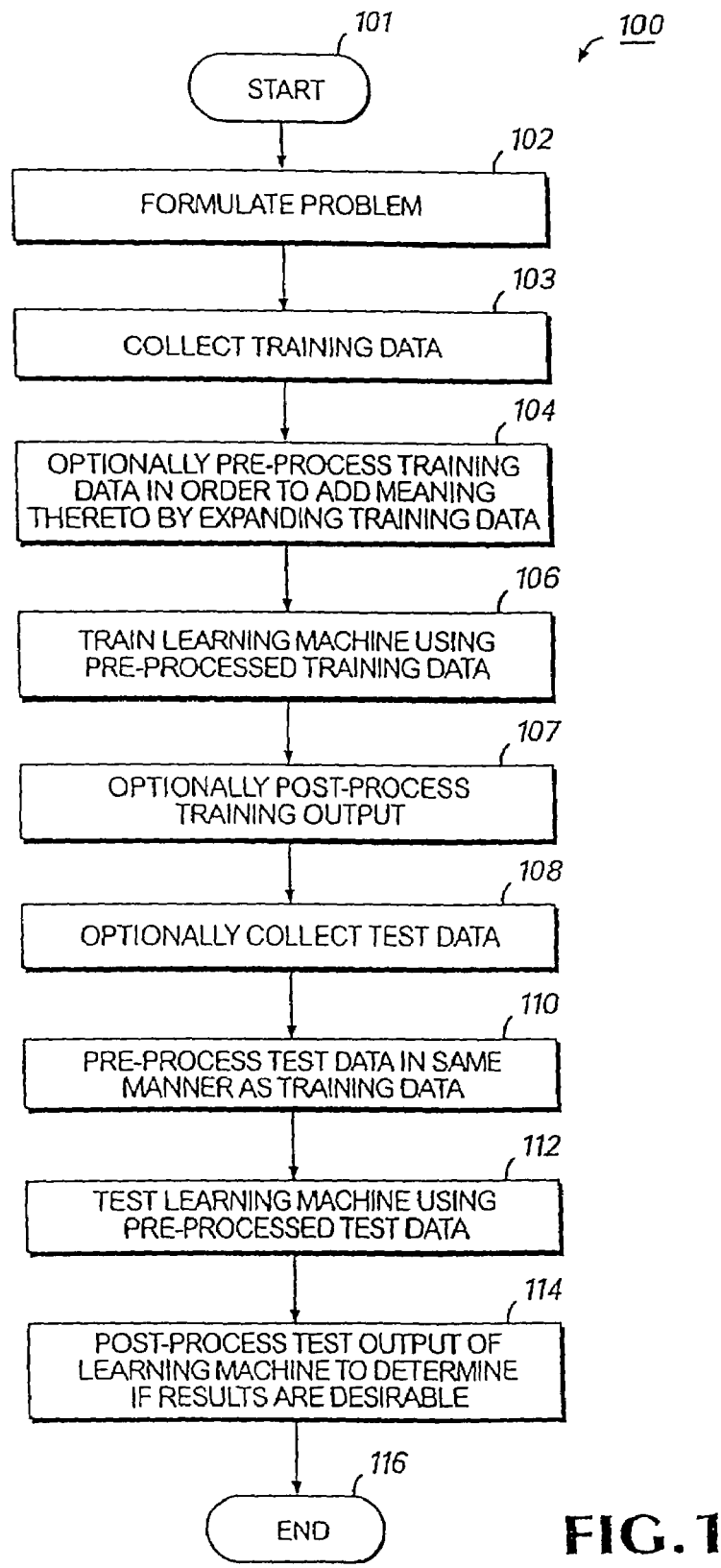
FIG. 1 is a flowchart illustrating an exemplary general method for analyzing data using a learning machine.

The following detailed description utilizes a number of acronyms which are generally well known in the art. While definitions are typically provided with the first instance of each acronym, for convenience, Table 1 below provides a list of the acronyms and abbreviations used herein along with their respective definitions.

TABLE 1

| ACRONYM | DESCRIPTION |
| --- | --- |
| ATAPI | attachment packet interface |
| CT | computed tomography |
| DMA | direct memory access |
| EIDE | enhanced integrated drive electronics |
| FFT | fast Fourier transform |
| I/O | input/output |
| IDE | integrated drive electronics |
| LAN | local area network |
| MRI | magnetic resonance imagining |
| PET | positron emission tomography |
| RAM | random access memory |
| ROM | read-only memory |
| SCSI | small computer system interface |
| SPECT | single-photon emission computed tomography |
| SVM | support vector machine |
| WAN | wide area network |

The present invention provides improved methods for analyzing images using learning machines. As used herein, the term "image" means the product of any imaging method, whether the image is obtained through conventional visual methods, e.g., photography, or by any other method of detecting an electromagnetic signal impinging on a recording medium or device, e.g., infrared radiation impinging on an infrared detector. Of particular interest in the described examples are the medical imaging methods, including but not limited to, x-ray, PET (positron emission tomography), MRI (magnetic resonance imaging), CT (computed tomography), SPECT (single-photon emission computed tomography), gamma camera, confocal microscopy (also referred to as "visual"), electrical impedance imaging, and ultrasound. For purposes of the present invention, the image can be derived ex vivo, e.g., a tissue sample viewed through a microscope, or in vivo, e.g., an x-ray projection image. For imaging methods that generate analog outputs, the analog output will have been digitized, either by digital scanning or by converting an analog signal into a digital signal such that input image to be analyzed according to the present invention is presumed to be in digital form.

While several examples of learning machines exist and advancements are expected in this field, the exemplary embodiments of the present invention focus on the support vector machine.

A first aspect of the present invention facilitates image analysis by optionally pre-processing the data prior to using the data to train a learning machine and/or optionally post-processing the output from a learning machine. Generally stated, pre-processing data comprises reformatting or augmenting the data in order to allow the learning machine to be applied most advantageously. For example, evaluation of one or more important characteristics within an image may involve pre-processing to create a bit map from the original gray scale image, or features of varying sizes may need to be converted, i.e., normalized, to a fixed dimensional form prior to processing in order to permit comparison of qualities such as contour, shape or density.

In a manner similar to pre-processing, post-processing involves interpreting the output of a learning machine in order to discover meaningful characteristics thereof. The meaningful characteristics to be ascertained from the output may be problem- or data-specific. Post-processing involves interpreting the output into a form that, for example, may be understood by or is otherwise useful to a human observer, or converting the output into a form which may be readily received by another device for, e.g., archival or transmission.

FIG. 1 is a flowchart illustrating a general method 100 for analyzing data using learning machines. The method 100 begins at starting block 101 and progresses to step 102 where a specific problem is formalized for application of analysis through machine learning. Particularly important is a proper formulation of the desired output of the learning machine. For instance, in predicting future performance of an individual equity instrument, or a market index, a learning machine is likely to achieve better performance when predicting the expected future change rather than predicting the future price level. The future price expectation can later be derived in a post-processing step as will be discussed later in this specification.

After problem formalization, step 103 addresses training data collection. Training data comprises a set of data points having known characteristics. Training data may be collected from one or more local and/or remote sources. The collection of training data may be accomplished manually or by way of an automated process, such as known electronic data transfer methods. Accordingly, an exemplary embodiment of the learning machine for use in conjunction with the present invention may be implemented in a networked computer environment. Exemplary operating environments for implementing various embodiments of the learning machine will be described in detail with respect to FIGS. 10-11.

At step 104, the collected training data is optionally pre-processed in order to allow the learning machine to be applied most advantageously toward extraction of the knowledge inherent to the training data. During this preprocessing stage the training data can optionally be expanded through transformations, combinations or manipulation of individual or multiple measures within the records of the training data. As used herein, "expanding data" is meant to refer to altering the dimensionality of the input data by changing the number of observations available to determine each input point (alternatively, this could be described as adding or deleting columns within a database table). By way of illustration, a data point may comprise the coordinates (1,4,9). An expanded version of this data point may result in the coordinates (1,1,4,2,9,3). In this example, it may be seen that the coordinates added to the expanded data point are based on a square-root transformation of the original coordinates. By adding dimensionality to the data point, this expanded data point provides a varied representation of the input data that is potentially more meaningful for analysis by a learning machine. Data expansion in this sense affords opportunities for learning machines to analyze data not readily apparent in the unexpanded training data.

Expanding data may comprise applying any type of meaningful transformation to the data and adding those transformations to the original data. The criteria for determining whether a transformation is meaningful may depend on the input data itself and/or the type of knowledge that is sought from the data. Illustrative types of data transformations include: addition of expert information; labeling; binary conversion, e.g., a bit map; transformations, such as Fourier, wavelet, Radon, principal component analysis and kernel principal component analysis, as well as clustering; scaling; normalizing; probabilistic and statistical analysis; significance testing; strength testing; searching for two-dimensional regularities; Hidden Markov Modeling; identification of equivalence relations; application of contingency tables; application of graph theory principles; creation of vector maps; addition, subtraction, multiplication, division, application of polynomial equations and other algebraic transformations; identification of proportionality; determination of discriminatory power; etc. In the context of medical data, potentially meaningful transformations include: association with known standard medical reference ranges; physiologic truncation; physiologic combinations; biochemical combinations; application of heuristic rules; diagnostic criteria determinations; clinical weighting systems; diagnostic transformations; clinical transformations; application of expert knowledge; labeling techniques; application of other domain knowledge; Bayesian network knowledge; etc. Specifically with regard to medical imaging, transformations can include segmentation techniques to recognize homogeneous regions within an image as distinct and belonging to different objects. Image segmentation techniques include histogram thresholding, edge-based segmentation, tree/graph based approaches, region growing, mass contraction, clustering, probabilistic or Bayesian approaches, neural networks for segmentation, and others. These and other transformations, as well as combinations thereof, will occur to those of ordinary skill in the art.

Those skilled in the art should also recognize that data transformations may be performed without adding dimensionality to the data points. For example a data point may comprise the coordinate (A, B, C). A transformed version of this data point may result in the coordinates (1, 2, 3), where the coordinate "1" has some known relationship with the coordinate "A," the coordinate "2" has some known relationship with the coordinate "B," and the coordinate "3" has some known relationship with the coordinate "C." A transformation from letters to numbers may be required, for example, if letters are not understood by a learning machine. Other types of transformations are possible without adding dimensionality to the data points, even with respect to data that is originally in numeric form. Furthermore, it should be appreciated that pre-processing data to add meaning thereto may involve analyzing incomplete, corrupted or otherwise "dirty" data. A learning machine cannot process "dirty" data in a meaningful manner. Thus, a pre-processing step may involve cleaning up or filtering a data set in order to remove, repair or replace dirty data points.

Returning to FIG. 1, the exemplary method 100 continues at step 106, where the learning machine is trained using the pre-processed data. As is known in the art, a learning machine is trained by adjusting its operating parameters until a desirable training output is achieved. The determination of whether a training output is desirable may be accomplished either manually or automatically by comparing the training output to the known characteristics of the training data. A learning machine is considered to be trained when its training output is within a predetermined error threshold from the known characteristics of the training data. In certain situations, it may be desirable, if not necessary, to post-process the training output of the learning machine at step 107. As mentioned, post-processing the output of a learning machine involves interpreting the output into a meaningful form. In the context of a regression problem, for example, it may be necessary to determine range categorizations for the output of a learning machine in order to determine if the input data points were correctly categorized. In the example of a pattern recognition problem, it is often not necessary to post-process the training output of a learning machine.

At step 108, test data is optionally collected in preparation for testing the trained learning machine. Test data may be collected from one or more local and/or remote sources. In practice, test data and training data may be collected from the same source(s) at the same time. Thus, test data and training data sets can be divided out of a common data set and stored in a local storage medium for use as different input data sets for a learning machine. Regardless of how the test data is collected, any test data used must be pre-processed at step 110 in the same manner as was the training data. As should be apparent to those skilled in the art, a proper test of the learning may only be accomplished by using testing data of the same format as the training data. Then, at step 112 the learning machine is tested using the pre-processed test data, if any. The test output of the learning machine is optionally post-processed at step 114 in order to determine if the results are desirable. Again, the post processing step involves interpreting the test output into a meaningful form. The meaningful form may be one that is readily understood by a human or one that is compatible with another processor. Regardless, the test output must be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations. The method 100 ends at step 116.

Figure 2:
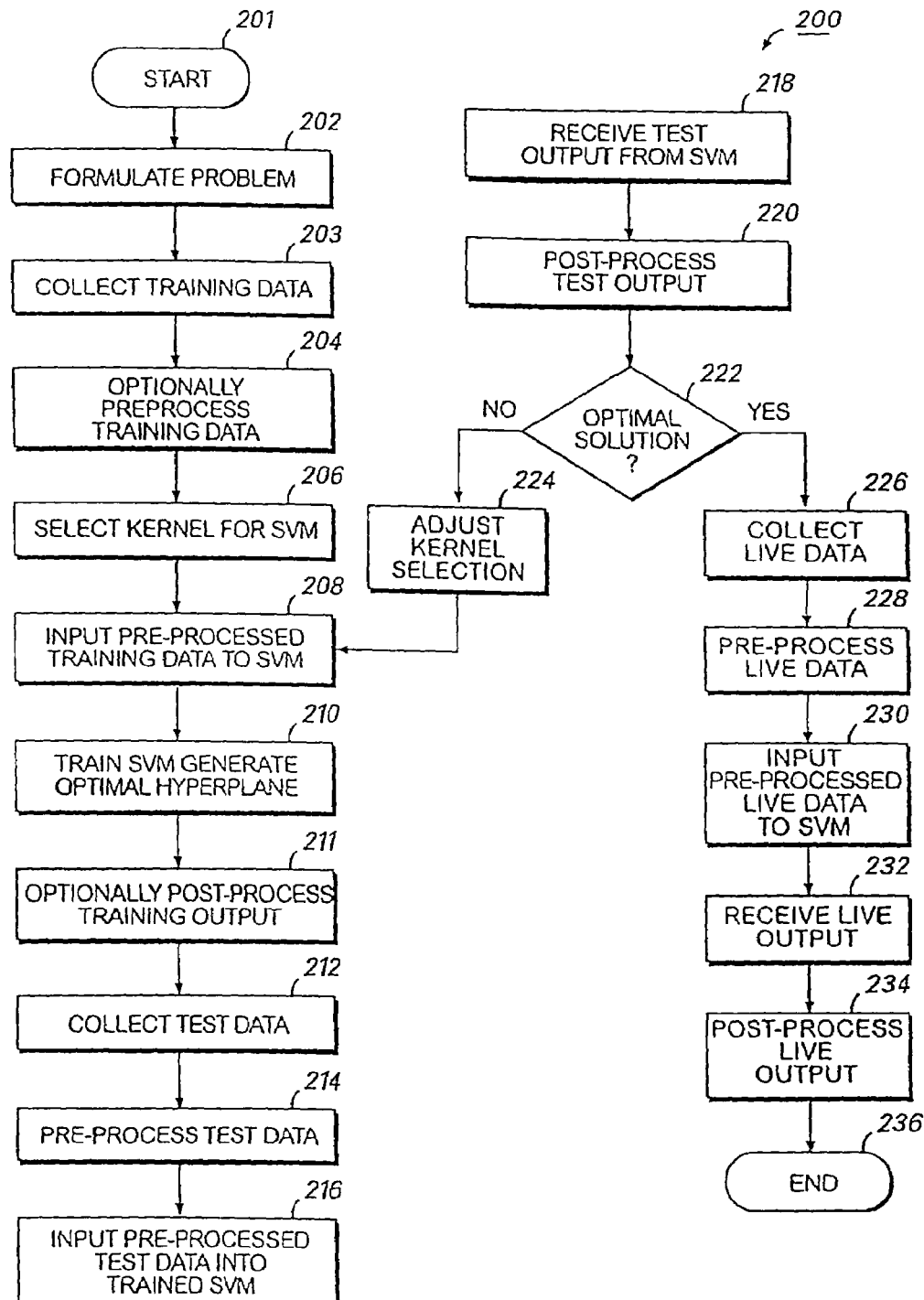
FIG. 2 is a flowchart illustrating an exemplary method for analyzing data using a support vector machine.

FIG. 2 is a flow chart illustrating an exemplary method 200 for enhancing knowledge that may be discovered from data using a specific type of learning machine known as a support vector machine (SVM). A SVM implements a specialized algorithm for providing generalization when estimating a multi-dimensional function from a limited collection of data. A SVM may be particularly useful in solving dependency estimation problems. More specifically, a SVM may be used accurately in estimating indicator functions (e.g. pattern recognition problems) and real-valued functions (e.g. function approximation problems, regression estimation problems, density estimation problems, and solving inverse problems). The SVM was originally developed by Boser, Guyon and Vapnik ("A training algorithm for optimal margin classifiers", *Fifth Annual Workshop on Computational Learning Theory*, Pittsburgh, ACM (1992) pp. 142-152). The concepts underlying the SVM are also explained in detail in Vapnik's book, entitled *Statistical Learning Theory* (John Wiley & Sons, Inc. 1998), which is herein incorporated by reference in its entirety. Accordingly, a familiarity with SVMs and the terminology used therewith are presumed throughout this specification.

The exemplary method 200 begins at starting block 201 and advances to step 202, where a problem is formulated and then to step 203, where a training data set is collected. As was described with reference to FIG. 1, training data may be collected from one or more local and/or remote sources, through a manual or automated process. At step 204 the training data is optionally pre-processed. Again, pre-processing data comprises enhancing meaning within the training data by cleaning the data, transforming the data and/or expanding the data. Those skilled in the art should appreciate that SVMs are capable of processing input data having extremely large dimensionality. In fact, the larger the dimensionality of the input data, the better the generalizations a SVM is able to calculate. Therefore, while training data transformations are possible that do not expand the training data, in the specific context of SVMs it is preferable that training data be expanded by adding meaningful information thereto.

At step 206 a kernel is selected for the SVM. As is known in the art, different kernels will cause a SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge. As is known in the art, exemplary kernels include polynomial kernels, radial basis classifier kernels, linear kernels, etc. In an alternate embodiment, a customized kernel may be created that is specific to a particular problem or type of data set. In yet another embodiment, the multiple SVMs may be trained and tested simultaneously, each using a different kernel. The quality of the outputs for each simultaneously trained and tested SVM may be compared using a variety of selectable or weighted metrics (see step 222) to determine the most desirable kernel. In a preferred embodiment for image processing, a Fourier kernel is selected to address issues of geometric shape recognition. This Fourier kernel, described in more detail below, is invariant under transformations of translation and rotation.

Next, at step 208 the pre-processed training data is input into the SVM. At step 210, the SVM is trained using the pre-processed training data to generate an optimal hyperplane. Optionally, the training output of the SVM may then be post-processed at step 211. Again, post-processing of training output may be desirable, or even necessary, at this point in order to properly calculate ranges or categories for the output. At step 212 test data is collected similarly to previous descriptions of data collection. The test data is pre-processed at step 214 in the same manner as was the training data above. Then, at step 216 the pre-processed test data is input into the SVM for processing in order to determine whether the SVM was trained in a desirable manner. The test output is received from the SVM at step 218 and is optionally post-processed at step 220.

Based on the post-processed test output, it is determined at step 222 whether an optimal minimum was achieved by the SVM. Those skilled in the art should appreciate that a SVM is operable to ascertain an output having a global minimum error. However, as mentioned above, output results of a SVM for a given data set will typically vary with kernel selection. Therefore, there are in fact multiple global minimums that may be ascertained by a SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by a SVM.

Accordingly, at step 222, determining whether the optimal minimum has been ascertained may involve comparing the output of a SVM with a historical or predetermined value. Such a predetermined value may be dependant on the test data set. For example, in the context of a pattern recognition problem where data points are classified by a SVM as either having a certain characteristic or not having the characteristic, a global minimum error of 50% would not be optimal. In this example, a global minimum of 50% is no better than the result that would be achieved by flipping a coin to determine whether the data point had that characteristic. As another example, in the case where multiple SVMs are trained and tested simultaneously with varying kernels, the outputs for each SVM may be compared with output of other SVM to determine the practical optimal solution for that particular set of kernels. The determination of whether an optimal solution has been ascertained may be performed manually or through an automated comparison process.

If it is determined that the optimal minimum has not been achieved by the trained SVM, the method advances to step 224, where the kernel selection is adjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method 200 is repeated from step 208, where the pre-processed training data is input into the SVM for training purposes. When it is determined at step 222 that the optimal minimum has been achieved, the method advances to step 226, where live data is collected similarly as described above. By definition, live data has not been previously evaluated, so that the desired output characteristics that were known with respect to the training data and the test data are not known.

At step 228 the live data is pre-processed in the same manner as was the training data and the test data. At step 230, the live pre-processed data is input into the SVM for processing. The live output of the SVM is received at step 232 and is post-processed at step 234. In one embodiment of the learning machine, post-processing comprises converting the output of the SVM into a computationally-derived alpha-numerical classifier for interpretation by a human or computer. Preferably, the alphanumerical classifier comprises a single value that is easily comprehended by the human or computer. The method 200 ends at step 236.

Figure 3:
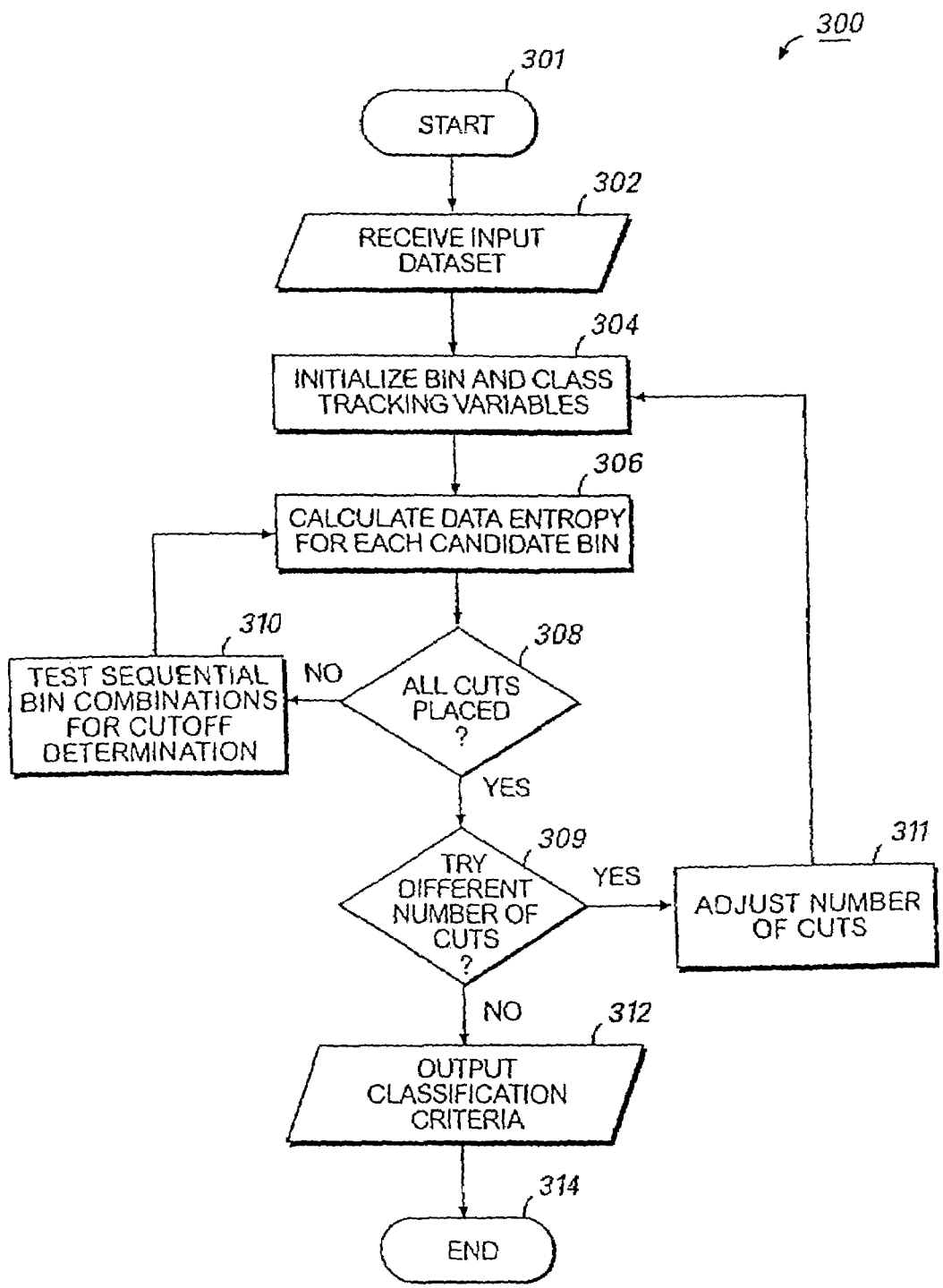
FIG. 3 is a flowchart illustrating an exemplary optimal categorization method that may be used in a stand-alone configuration or in conjunction with a learning machine for pre-processing or post-processing techniques.

FIG. 3 is a flow chart illustrating an exemplary optimal categorization method 300 that may be used for pre-processing data or post-processing output from a learning machine. Additionally, as will be described below, the exemplary optimal categorization method may be used as a stand-alone categorization technique, independent from learning machines. The exemplary optimal categorization method 300 begins at starting block 301 and progresses to step 302, where an input data set is received. The input data set comprises a sequence of data samples from a continuous variable. The data samples fall within two or more classification categories. Next, at step 304 the bin and class-tracking variables are initialized. As is known in the art, bin variables relate to resolution, while class-tracking variables relate to the number of classifications within the data set. Determining the values for initialization of the bin and class-tracking variables may be performed manually or through an automated process, such as a computer program for analyzing the input data set. At step 306, the data entropy for each bin is calculated. Entropy is a mathematical quantity that measures the uncertainty of a random distribution. In the exemplary method 300, entropy is used to gauge the gradations of the input variable so that maximum classification capability is achieved.

The method 300 produces a series of "cuts" on the continuous variable, such that the continuous variable may be divided into discrete categories. The cuts selected by the exemplary method 300 are optimal in the sense that the average entropy of each resulting discrete category is minimized. At step 308, a determination is made as to whether all cuts have been placed within input data set comprising the continuous variable. If all cuts have not been placed, sequential bin combinations are tested for cutoff determination at step 310. From step 310, the exemplary method 300 loops back through step 306 and returns to step 308 where it is again determined whether all cuts have been placed within input data set comprising the continuous variable. When all cuts have been placed, the entropy for the entire system is evaluated at step 309 and compared to previous results from testing more or fewer cuts. If it cannot be concluded that a minimum entropy state has been determined, then other possible cut selections must be evaluated and the method proceeds to step 311. From step 311 a heretofore untested selection for number of cuts is chosen and the above process is repeated from step 304. When either the limits of the resolution determined by the bin width has been tested or the convergence to a minimum solution has been identified, the optimal classification criteria is output at step 312 and the exemplary optimal categorization method 300 ends at step 314.

The optimal categorization method 300 takes advantage of dynamic programming techniques. As is known in the art, dynamic programming techniques may be used to significantly improve the efficiency of solving certain complex problems through carefully structuring an algorithm to reduce redundant calculations. In the optimal categorization problem, the straightforward approach of exhaustively searching through all possible cuts in the continuous variable data would result in an algorithm of exponential complexity and would render the problem intractable for even moderate sized inputs. By taking advantage of the additive property of the target function, in this problem the average entropy, the problem may be divided into a series of sub-problems. By properly formulating algorithmic sub-structures for solving each sub-problem and storing the solutions of the sub-problems, a significant amount of redundant computation may be identified and avoided. As a result of using the dynamic programming approach, the exemplary optimal categorization method 300 may be implemented as an algorithm having a polynomial complexity, which may be used to solve large sized problems.

As mentioned above, the exemplary optimal categorization method 300 may be used in pre-processing data and/or post-processing the output of a learning machine. For example, as a pre-processing transformation step, the exemplary optimal categorization method 300 may be used to extract classification information from raw data. As a post-processing technique, the exemplary optimal range categorization method may be used to determine the optimal cut-off values for markers objectively based on data, rather than relying on ad hoc approaches. As should be apparent, the exemplary optimal categorization method 300 has applications in pattern recognition, classification, regression problems, etc. The exemplary optimal categorization method 300 may also be used as a stand-alone categorization technique, independent from SVMs and other learning machines. An exemplary stand-alone application of the optimal categorization method 300 will be described with reference to FIG. 7.

In an example of pre-processing of data use in image analysis, image segmentation provides means for isolating objects from the background to emphasize the salient features of the original image. Quite often, particularly in medical applications, two or more objects may be overlapped or clustered together. For example, in two-dimensional gel image analysis, several spots can cluster together. In cell imaging, cells can overlap. In mammograms, calcifications and masses can overlap. In such cases, separation of the objects is crucial in an effective analysis system.

Referring to FIG. 5a, two partially overlapping masses 502, 504 represented as a gray scale image are illustrated. In an exemplary embodiment, a "gravitation" model is iteratively applied to the gray scale image to contract the masses. In the digital image, pixel values are viewed as "mass" values, and gravitational forces among the masses are used for the contraction movements. The process is analogous to the process of star and planet formation. The initially wide spread masses 502, 504 are contracted under the gravitation model toward the respective centroids to produce two dense, well-formed bodies shown in FIG. 5b as 502' and 504'. This approach is driven by the natural patterns in the image itself. No prior information about the specifics of the image is required. The gravitation model is insensitive to noise and outliers, and is generic in that it is applicable to different types of images by simply adjusting the threshold for pixel movements. In general principle, the gravitation model might be considered an inverse of region growing algorithms which are known in image segmentation, however, instead of expanding from a "seed", the object contracts into a "seed" so that distinct seeds can be identified. Alternatively, other known image segmentation algorithms may be used to pre-process the image data to enhance the image analysis process.

FIG. 4 illustrates an exemplary unexpanded data set 400 that may be used as input for a support vector machine. This data set 400 is referred to as "unexpanded" because no additional information has been added thereto. As shown, the unexpanded data set comprises a training data set 402 and a test data set 404. Both the unexpanded training data set 402 and the unexpanded test data set 404 comprise data points, such as exemplary data point 406, relating to historical clinical data from sampled medical patients. In this example, the data set 400 may be used to train a SVM to determine whether a breast cancer patient will experience a recurrence or not.

Each data point includes five input coordinates, or dimensions, and an output classification shown as 406a-f which represent medical data collected for each patient. In particular, the first coordinate 406a represents "Age," the second coordinate 406b represents "Estrogen Receptor Level," the third coordinate 406c represents "Progesterone Receptor Level," the fourth coordinate 406d represents "Total Lymph Nodes Extracted," the fifth coordinate 406e represents "Positive (Cancerous) Lymph Nodes Extracted," and the output classification 406f, represents the "Recurrence Classification." The important known characteristic of the data 400 is the output classification 406f (Recurrence Classification), which, in this example, indicates whether the sampled medical patient responded to treatment favorably without recurrence of cancer ("−1") or responded to treatment negatively with recurrence of cancer ("1"). This known characteristic will be used for learning while processing the training data in the SVM will be used in an evaluative fashion after the test data is input into the SVM thus creating a "blind" test, and will obviously be unknown in the live data of current medical patients.

Table 2 provides an exemplary test output from a SVM trained with the unexpanded training data set 402 and tested with the unexpanded data set 404 shown in FIG. 4.

TABLE 2

Vapnik's Polynomial

Alphas bounded up to 1000
Input values will be individually scaled to lie between 0 and 1
SV zero threshold: 1e−16
Margin threshold: 0.1
Objective zero tolerance: 1e−17
Degree of polynomial: 2
Test set:

Total samples: 24
Positive samples: 8
False negatives: 4
Negative samples: 16
False positives: 6

The test output has been post-processed to be comprehensible by a human or computer. According to the table, the test output shows that 24 total samples (data points) were examined by the SVM and that the SVM incorrectly identified four of eight positive samples (50%), i.e., found negative for a positive sample, and incorrectly identified 6 of sixteen negative samples (37.5%), i.e., found positive for a negative sample.

Figure 6:
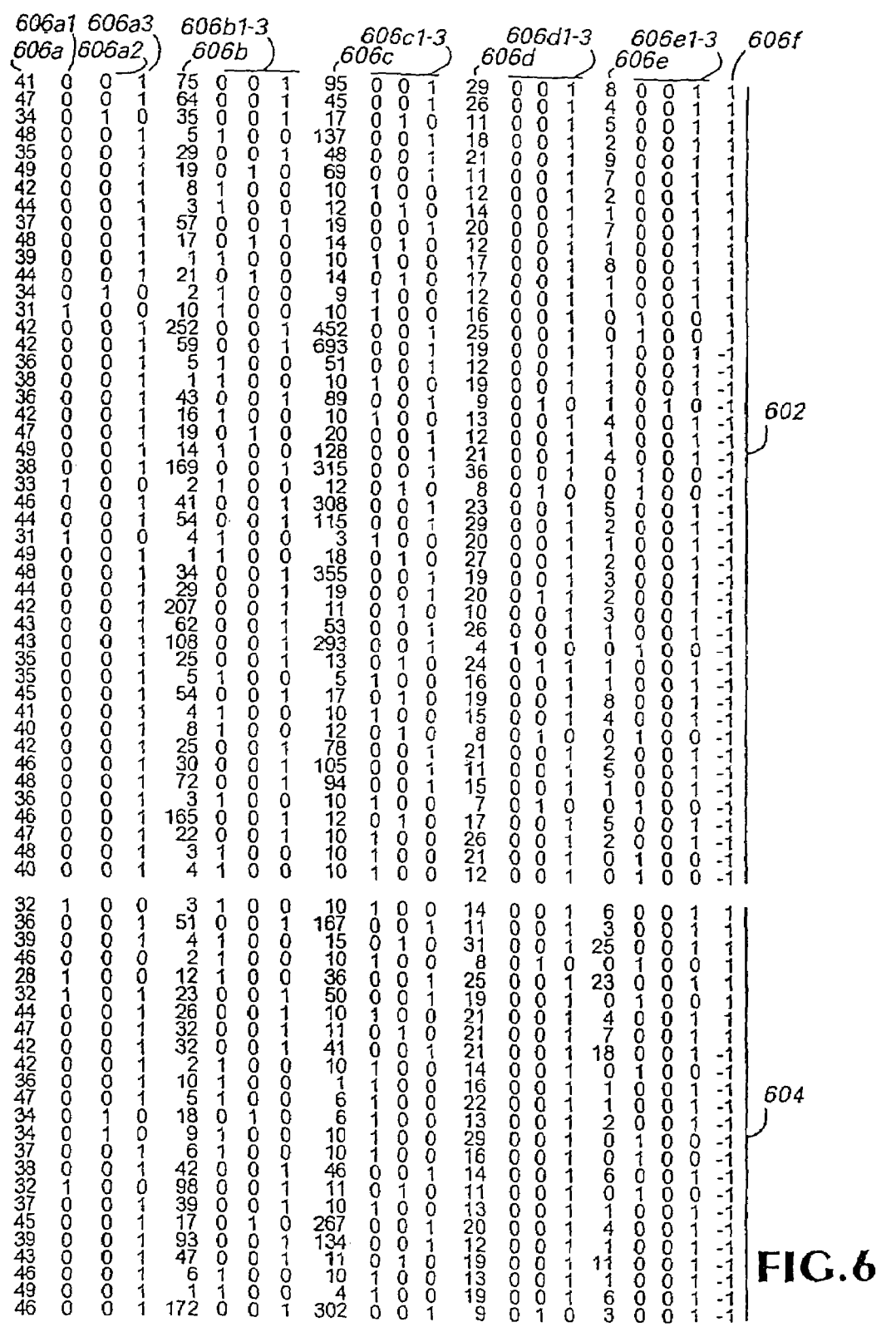

FIG. 6 illustrates an exemplary expanded data set 600 that may be used as input for a support vector machine. This data set 600 is referred to as "expanded" because additional information has been added thereto. Note that aside from the added information, the expanded data set 600 is identical to the unexpanded data set 400 shown in FIG. 4. The additional information supplied to the expanded data set has been supplied using the exemplary optimal range categorization method 300 described with reference to FIG. 3. As shown, the expanded data set comprises a training data set 602 and a test data set 604. Both the expanded training data set 602 and the expanded test data set 604 comprise data points, such as exemplary data point 606, relating to historical data from sampled medical patients. Again, the data set 600 may be used to train a SVM to learn whether a breast cancer patient will experience a recurrence of the disease.

Through application of the exemplary optimal categorization method 300, each expanded data point includes twenty coordinates (or dimensions) 606a1-3 through 606e1-3, and an output classification 606f, which collectively represent medical data and categorization transformations thereof for each patient. In particular, the first coordinate 606a represents "Age," the second coordinate through the fourth coordinate 606a1-606a3 are variables that combine to represent a category of age. For example, a range of ages may be categorized, for example, into "young" "middle-aged" and "old" categories respective to the range of ages present in the data. As shown, a string of variables "0" (606a1), "0" (606a2), "1" (606a3) may be used to indicate that a certain age value is categorized as "old." Similarly, a string of variables "0" (606a1), "1" (606a2), "0" (606a3) may be used to indicate that a certain age value is categorized as "middle-aged." Also, a string of variables "1" (606a1), "0" (606a2), "0" (606a1) maybe used to indicate that a certain age value is categorized as "young." From an inspection of FIG. 6, it may be seen that the optimal categorization of the range of "Age" 606a values, using the exemplary method 300, was determined to be 31-33="young," 34="middle-aged" and 35-49="old." The other coordinates, namely coordinate 606b "Estrogen Receptors Level," coordinate 606c "Progesterone Receptor Level," coordinate 606d "Total Lymph Nodes Extracted," and coordinate 606e "Positive (Cancerous) Lymph Nodes Extracted," have each been optimally categorized in a similar manner.

Table 3 provides an exemplary expanded test output from a SVM trained with the 30 expanded training data set 602 and tested with the expanded data set 604 shown in FIG. 6.

TABLE 3

Vapnik's Polynomial

Alphas bounded up to 1000
Input values will be individually scaled to lie between 0 and 1
SV zero threshold: 1e-16
Margin threshold: 0.1
Objective zero tolerance: 1e-17
Degree of polynomial: 2
Test set:

Total samples: 24
Positive samples: 8
False negatives: 4
Negative samples: 16
False positives: 4

The expanded test output has been post-processed to be comprehensible by a human or computer. As indicated, the expanded test output shows that 24 total samples (data points) were examined by the SVM and that the SVM incorrectly identified four of eight positive samples (50%) and incorrectly identified four of sixteen negative samples (25%). Accordingly, by comparing this expanded test output with the unexpanded test output of Table 2, it may be seen that the expansion of the data points leads to improved results (i.e. a lower global minimum error), specifically a reduced instance of patients who would unnecessarily be subjected to follow-up cancer treatments.

Figure 7:
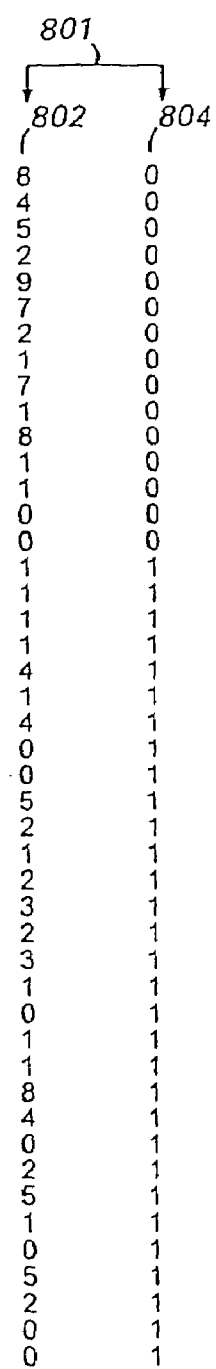
FIG. 7 illustrates an exemplary input data set for a standalone application of the optimal categorization method of FIG. 3.
Figure 8:
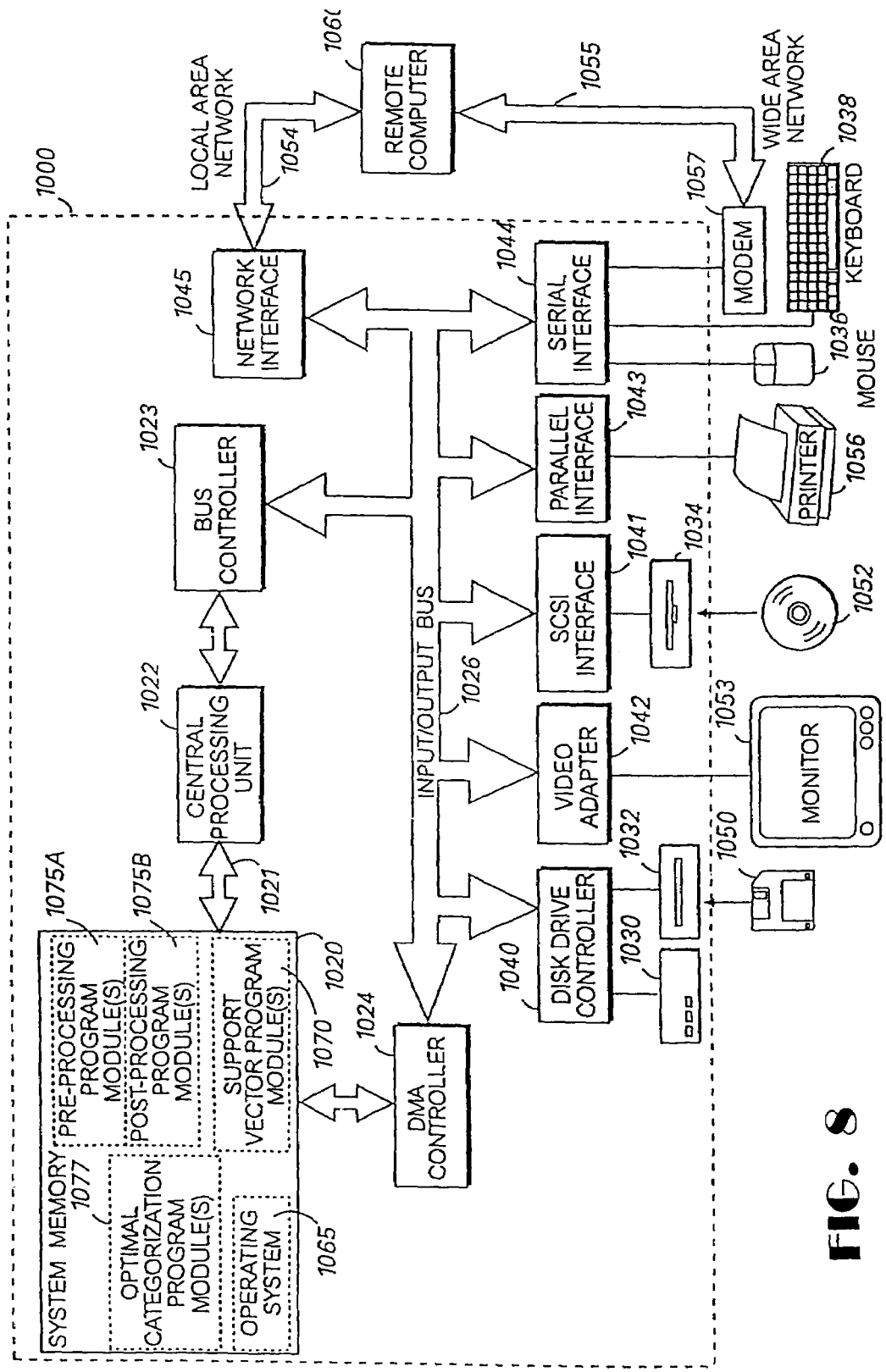
FIG. 8 is a functional block diagram illustrating an exemplary operating environment for an exemplary embodiment of the present invention.

FIG. 7 illustrates an exemplary input and output for a stand alone application of the optimal categorization method 300 described in FIG. 3. In the example of FIG. 8, the input data set 801 comprises a "Number of Positive Lymph Nodes" 802 and a corresponding "Recurrence Classification" 804. In this example, the optimal categorization method 300 has been applied to the input data set 801 in order to locate the optimal cutoff point for determination of treatment for cancer recurrence, based solely upon the number of positive lymph nodes collected in a post-surgical tissue sample. The well-known clinical standard is to prescribe treatment for any patient with at least three positive nodes. However, the optimal categorization method 300 demonstrates that the optimal cutoff, seen in Table 4, based upon the input data 801, should be at the higher value of 5.5 lymph nodes, which corresponds to a clinical rule prescribing follow-up treatments in patients with at least six positive lymph nodes.

TABLE 4

Number of subintervals: 2
Number of classes: 2
Number of data points: 46
Lower bound: -1
Upper bound: 10

TABLE 4-continued

Number of bins: 22
Regularization constant: 1
Data file: posnodes.prn
Min. Entropy -0.568342
Optimal cut-off: 5.500000

As shown in Table 5 below, the prior art accepted clinical cutoff point (≧3.0) resulted in 47% correctly classified recurrences and 71% correctly classified non-recurrences.

TABLE 5

| Cut Point | Correctly Classified Recurrence | Correctly Classified Non-Recurrence |
|---|---|---|
| Clinical (≧3.0) | 7 of 15 (47%) | 22 of 31 (71%) |
| Optimal (≧5.5)) | 5 of 15 (33%) | 30 of 31 (97%) |

Accordingly, 53% of the recurrences were incorrectly classified (further treatment was improperly not recommended) and 29% of the non-recurrences were incorrectly classified (further treatment was incorrectly recommended). By contrast, the cutoff point determined by the optimal categorization method 300 (≧5.5) resulted in 33% correctly classified recurrences and 97% correctly classified non-recurrences. Accordingly, 67% of the recurrences were incorrectly classified (further treatment was improperly not recommended) and 3% of the non-recurrences were incorrectly classified (further treatment was incorrectly recommended).

As shown by this example, it may be feasible to attain a higher instance of correctly identifying those patients who can avoid the post-surgical cancer treatment regimes, using the exemplary optimal categorization method 300. Even though the cutoff point determined by the optimal categorization method 300 yielded a moderately higher percentage of incorrectly classified recurrences, it yielded a significantly lower percentage of incorrectly classified non-recurrences. Thus, considering the trade-off, and realizing that the goal of the optimization problem was the avoidance of unnecessary treatment, the results of the cutoff point determined by the optimal categorization method 300 are mathematically superior to those of the prior art clinical cutoff point. This type of information is potentially extremely useful in providing additional insight to patients weighing the choice between undergoing treatments such as chemotherapy or risking a recurrence of breast cancer.

Table 6 is a comparison of exemplary post-processed output from a first support vector machine comprising a linear kernel and a second support vector machine comprising a polynomial kernel.

TABLE 6

| I. Simple Dot Product | II. Vapnik's Polynomial |
|---|---|
| Alphas bounded up to 1000. Input values will not be scaled. SV zero threshold: 1e-16 Margin threshold: 0.1 Objective zero tolerance: 1e-07 | Alphas bounded up to 1000. Input values will not be scaled. SV zero threshold: 1e-16 Margin threshold: 0.1 Objective zero tolerance: 1e-07 Degree of polynomial: 2 |
| Test set | Test set |
| Total samples: 24 | Total samples: 24 |

TABLE 6-continued

| | |
|---|---|
| Positive samples: 8 | Positive samples: 8 |
| False negatives: 6 | False negatives: 2 |
| Negative samples: 16 | Negative samples: 16 |
| False positives: 3 | False positives: 4 |

Table 6 demonstrates that a variation in the selection of a kernel may affect the level of quality of the output of a SVM. As shown, the post-processed output of a first SVM (Column I) comprising a linear dot product kernel indicates that for a given test set of twenty four samples, six of eight positive samples were incorrectly identified and three of sixteen negative samples were incorrectly identified. By way of comparison, the post-processed output for a second SVM (Column II) comprising a polynomial kernel indicates that for the same test set, only two of eight positive samples were incorrectly identified and four of sixteen negative samples were identified. By way of comparison, the polynomial kernel yielded significantly improved results pertaining to the identification of positive samples and yielded only slightly worse results pertaining to the identification of negative samples. Thus, as will be apparent to those of skill in the art, the global minimum error for the polynomial kernel is lower than the global minimum error for the linear kernel for this data set.

FIG. 8 and the following discussion are intended to provide a brief and general description of a suitable computing environment for implementing the computer-aided image analysis of the present invention. Although the system shown in FIG. 8 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (Integrated Drive Electronics, i.e., a hard disk drive interface for PCs), ATAPI (ATtAchment Packet Interface, i.e., CD-ROM and tape drive interface), or EIDE (Enhanced IDE) interface may be associated with an optical drive such as may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the learning machine may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm according to the exemplary methods described with reference to FIGS. 1 and 2. Furthermore, optimal categorization program modules 1077 may comprise computer-executable instructions for optimally categorizing a data set according to the exemplary methods described with reference to FIG. 3.

The computer 1000 may operate in a networked environment using logical connections to one or more remote computers, such as remote computer 1060. The remote computer 1060 may be a server, a router, a peer device or other common network node, and typically includes many or all of the elements described in connection with the computer 1000. In a networked environment, program modules and data may be stored on the remote computer 1060. The logical connections depicted in FIG. 8 include a local area network ("LAN") 1054 and a wide area network ("WAN") 1055. In a LAN environment, a network interface 1045, such as an Ethernet adapter card, can be used to connect the computer 1000 to the remote computer 1060. In a WAN environment, the computer 1000 may use a telecommunications device, such as a modem 1057, to establish a connection. It will be appreciated that the network connections shown are illustrative and other devices of establishing a communications link between the computers may be used.

In another embodiment, a plurality of SVMs can be configured to hierarchically process multiple data sets in parallel or sequentially. In particular, one or more first-level SVMs may be trained and tested to process a first type of data and one or more first-level SVMs can be trained and tested to process a second type of data. Additional types of data may be processed by other first-level SVMs. The output from some or all of the first-level SVMs may be combined in a logical manner to produce an input data set for one or more second-level SVMs. In a similar fashion, output from a plurality of second-level SVMs may be combined in a logical manner to produce input data for one or more third-level SVM. The hierarchy of SVMs may be expanded to any number of levels as may be appropriate. In this manner, lower hierarchical level SVMs may be used to pre-process data that is to be input into higher level SVMs. Also, higher hierarchical level SVMs may be used to post-process data that is output from lower hierarchical level SVMs.

Each SVM in the hierarchy or each hierarchical level of SVMs may be configured with a distinct kernel. For example, SVMs used to process a first type of data maybe configured with a first type of kernel while SVMs used to process a second type of data may utilize a second, different type of kernel. In addition, multiple SVMs in the same or different hierarchical level may be configured to process the same type of data using distinct kernels.

Figure 9:
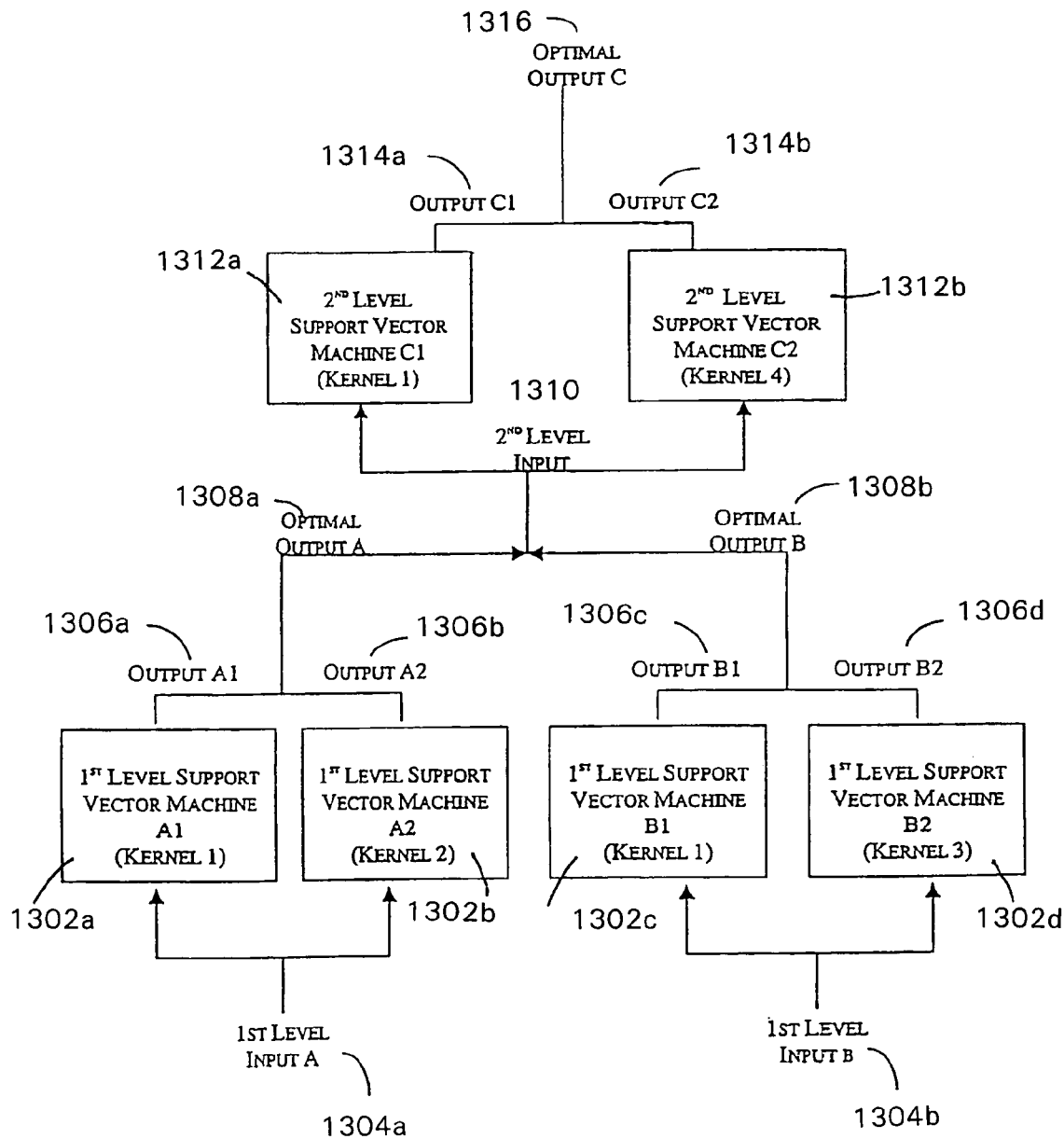
FIG. 9 is a functional block diagram illustrating a hierarchical system of multiple support vector machines.

FIG. 9 is presented to illustrate an exemplary hierarchical system of SVMs. As shown, one or more first-level SVMs 1302a and 1302b may be trained and tested to process a first type of input data 1304a, such as mammography data, pertaining to a sample of medical patients. One or more of these SVMs may comprise a distinct kernel, indicated as "KERNEL 1" and "KERNEL 2". Also, one or more additional first-level SVMs 1302c and 1302d may be trained and tested to process a second type of data 1304b, which may be, for example, genomic data or images of cytology specimens, for the same or a different sample of medical patients. Again, one or more of the additional SVMs may comprise a distinct kernel, indicated as "KERNEL 1" and "KERNEL 3". The output from each of the like first-level SVMs may be compared with each other, e.g., 1306a compared with 1306b; 1306c compared with 1306d, in order to determine optimal outputs 1308a and 1308b. Then, the optimal outputs from the two groups or first-level SVMs, i.e., outputs 1308a and 1308b, maybe combined to form a new multi-dimensional input data set 1310, for example, relating to mammography and genomic data. The new data set may then be processed by one or more appropriately trained and tested second-level SVMs 1312a and 1312b. The resulting outputs 1314a and 1314b from second-level SVMs 1312a and 1312b may be compared to determine an optimal output 1316. Optimal output 1316 may identify causal relationships between the mammography and genomic data points. As should be apparent to those of skill in the art, other combinations of hierarchical SVMs may be used to process either in parallel or serially, data of different types in any field or industry in which analysis of data is desired.

In application to image analysis, multiple SVMs are used to process data of different types that can be extracted from a digitized image. The different types of data can comprise different characteristics or qualities of objects found in the image, for example, size, shape, density, quantity, orientation, etc. The following example provides an illustrative application of multiple SVMs to image analysis, particularly for analysis of mammograms for diagnosis of breast cancer.

Calcification in breast tissue is of concern because of its association, in certain configurations, with carcinoma. Computer-aided detection and classification of microcalcifications identified by mammography has been an important area of focus in the field of image analysis. (See, e.g., Abstracts from IWDM 2000—Fifth International Workshop on Digital Mammography.) Since a significant percentage of normal screening mammograms show some calcification, mere detection of all calcification provides little benefit since not all types of calcification have the same clinical significance. Generally speaking, microcalcifications are associated with a malignant process and macrocalcifications are associated with a benign process. However, other characteristics of the calcifications can indicate association with either a benign or malignant structure, including shape, number and distribution. Therefore, the ability to distinguish between benign calcifications and those associated with cancer is key to successful computer-aided image analysis of mammograms.

Figure 10:
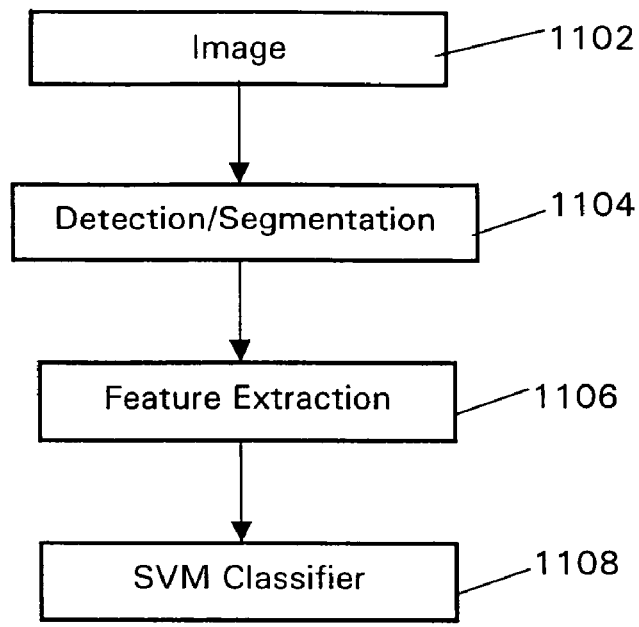
FIG. 10 is a functional block diagram illustrating a basic process flow for image analysis using support vector machines.

Two additional categories of suspicious abnormalities that may be seen in mammograms which indicate the possible presence of a malignancy are masses and structural distortions. Masses are three-dimensional lesions which may represent a localizing sign of cancer. Masses are described by their location, size, shape, margin characteristics, x-ray attenuation (radiodensity), and effect on surrounding tissue. Structural distortions are focal disruptions of the normal tissue patterns. Radiographically, distortions appear as surrounding tissue being "pulled inward" into a focal point FIG. 10 provides a flowchart of the basic analysis sequence according to the present invention for mammogram analysis using SVMs. The digitized mammogram image 1102 is input into the processor where the detection component 1104 finds the areas (objects) of particular interest in the image 1102 and, by segmentation, separates these objects from the background. The feature extraction component 1106 formulates numerical values relevant to the classification task from the segmented objects. The SVM classifier 1108 produces an index discriminating between the benign and malignant cases.

Figure 11:
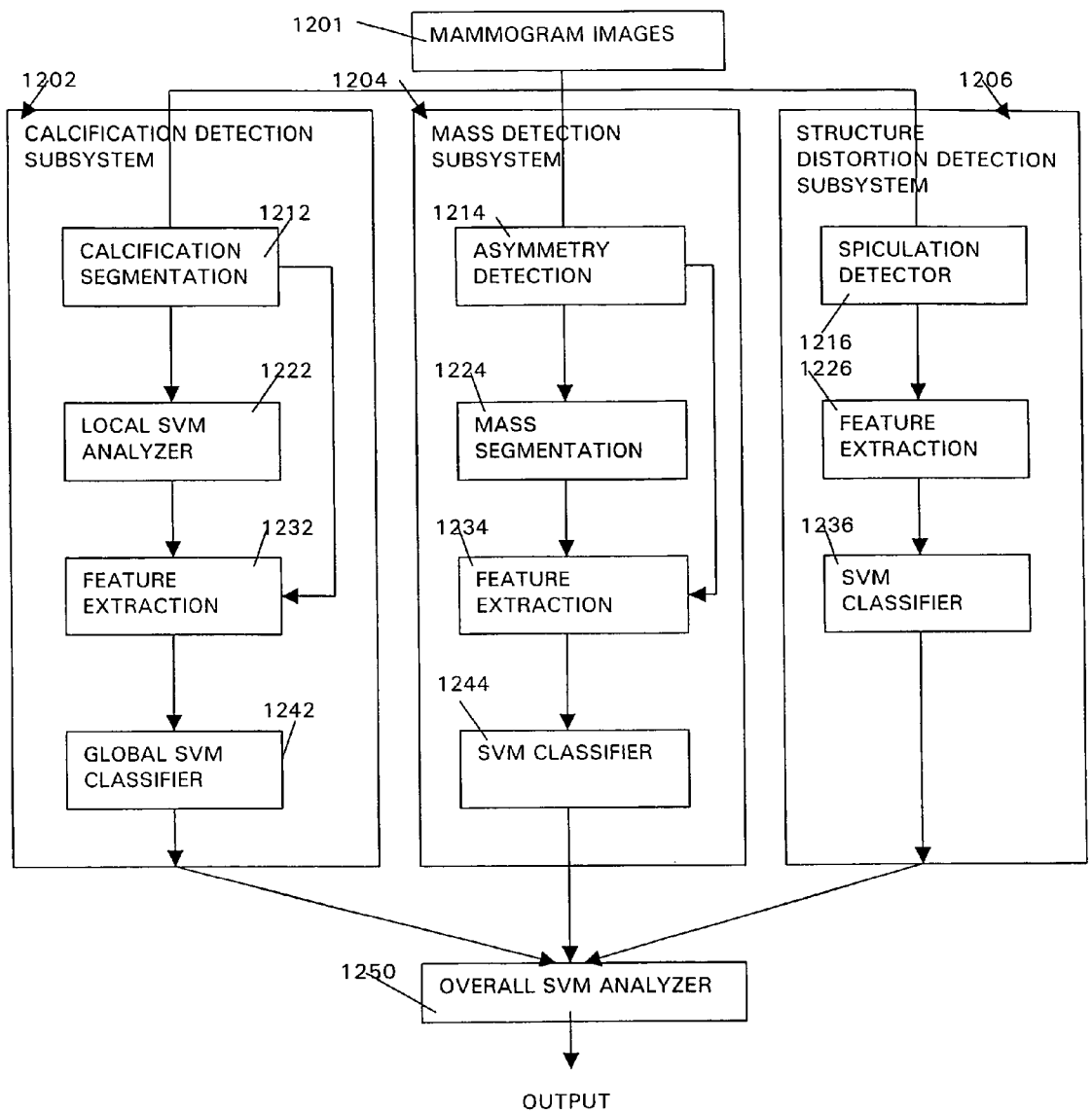
FIG. 11 is a functional block diagram illustrating an exemplary image analysis system with multiple detection subsystems for use in analysis of mammograms.

Implementation of the exemplary embodiment of the inventive image analysis system and method for mammogram analysis employs three SVM-based detection subsystems for calcifications 1202, masses 1204 and structural distortions 1206, each of which receives the digitized mammogram images 1201 as input, as shown in FIG. 11. Although each of the three subsystems was developed separately, the basic structure of each subsystem is similar. The outputs of the three subsystems are input into a separate SVM 1250 which performs overall analysis and provides the final output, which in this case, would be a diagnosis indicating the presence or absence of a malignancy.

In each of the three subsystems, the detection component finds the areas of particular interest in the image and separates the objects from the background. The feature extraction component formulates numerical values relevant to the classification task from the segmented objects. The SVM classifier produces an index discriminating between the benign and malignant cases.

The individual components can be developed in parallel due to their modular structure. (See, e.g., module 1070 in FIG. 8.) For example, in developing the calcification segmentation component 1202, a selected set of malignant, benign, and normal cases representing a wide range of images was used to guide and test the design in order to produce a general, robust and accurate algorithm. At the same time, the SVM classifier 1242 was developed and tested with manually prepared input data. A set of 300 images (150 benign and 150 malignant cases) was used in training the SVM. An independent set of 328 images was used for testing. High dimensional input features were used to ensure a sufficient capacity for automatically extracted features. The components will be integrated and adjusted for optimal performance.

In calcification detection subsystem 1202, the first step in finding calcifications is to process the image data to find the bright spots on the mammogram, i.e., to segment the calcifications (step 1212). In the preferred embodiment, the method involves finding local extremes of 2-dimensional discrete function F (x, y). Given that the mammogram consists of gray scale images, the problem involves distinguishing between the white and black spots in the image. The conventional method of solving this problem is to determine for each point (x, y), e.g., each pixel, that the value F(x, y) in any one point is not less then the value in every neighbor point. Images in the computer have eight neighbors for every point (pixel). Another existing method for identifying local minima and maxima involves applying a Gaussian filter to every point (x, y) where the function F(x, y) is determined. Other methods of solving the problem involve finding the local extremes, however, all of the known methods 1) require a number of calculations to be performed at each point, and 2) must be applied to each and every point (pixel) in the image. As a result, these algorithms can be very time consuming.

Figure 12:
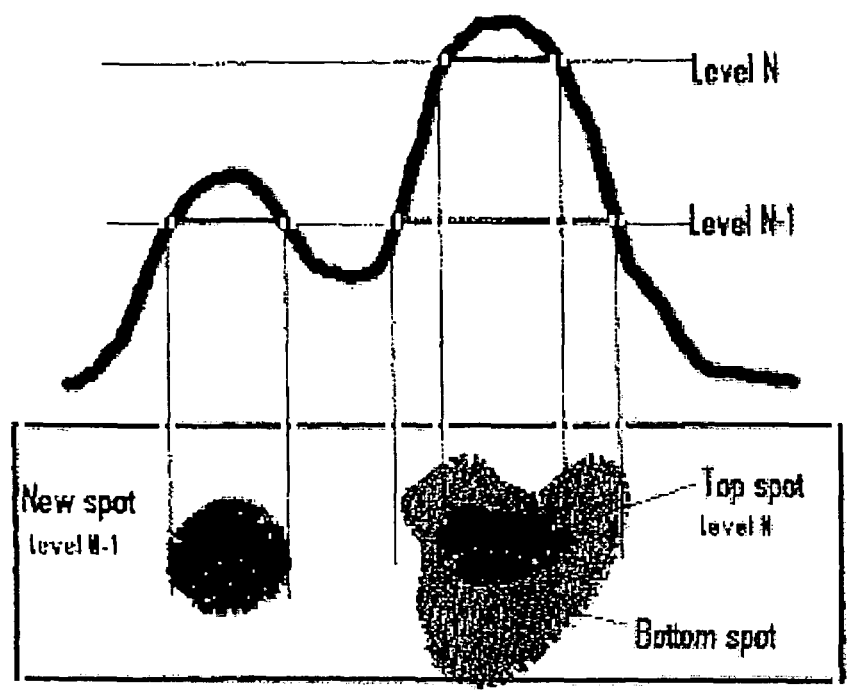
FIG. 12 is a combined curve and bit mapped image illustrating mapping of gray levels to a gray level curve.

In one aspect of the present invention, a method for finding local extremes of 2-dimensional discrete function avoids the examination of all points (x, y) and, therefore, dramatically reduces the processing time. Specifically, local maxima and minima are determined by using spots in the image rather than performing a pixel-by-pixel evaluation of brightness. The spots in the image are compared against a series of brightness thresholds to generate a plurality of bitmaps. The method can be illustrated using the case of the gray scale image shown in FIG. 12 as an example. By definition, the brightness of the image $F(x_i, y_j)$ in the computer is a discrete function. Brightness can be further discriminated by decreasing the number of levels of brightness to N (for example, N=32, or 16, or any other value). The gray image is then transformed into a set of N binary (black ("1") and white ("0")) images (bitmaps). At bitmap L (L=1, 2, ..., N) the pixel is black if the brightness of the corresponding pixel at the initial image F is greater than $F_L$, where $F_L=(L-1)-(F_{max}-F_{min})/N$. Otherwise, the pixel is white. Referring to FIG. 12, the dark center of the right-hand image is mapped to the highest level bitmap ("level N") and corresponds to the local maximum. The next lower level bitmap ("level N−1") defines another threshold such that the values on the curve above level N−1 are dark for the N−1 level bitmap. This results in identification of two types of spots—those that have values above level N and those that have values above level N−1, such that spots with brightness levels exceeding level N will also be included in the level N−1 bitmap. To differentiate the spots, the two bitmaps (from level N and level N−1) are superimposed. Spots of the first type are spots on level N−1, referred to as "bottom spots." The remaining spots on the level N−1 bitmap represent the "top spots", as indicated in FIG. 12. The bottom spots represent slopes of the curves for the local maxima of the top spots. This process is repeated by superimposing the bitmap from the level N−2 with the bitmap from the level N−1 to identify new top spots and bottom spots at these levels, e.g. the (N−1) top spot and the (N−2) bottom spot. This process is further repeated until all local maxima, i.e. top spots, and bottom spots for each of the N levels are found, thus avoiding the need to perform a pixel-by-pixel analysis of the image.

Calcifications can be classified by describing the geometry of the bright spots. The method of analyzing the geometry of the spots is based on the bitmaps described above for rapid calculation of continuing characteristics. For example, the gradients of slopes corresponding to the spots can be analyzed to distinguish certain background features. It is known that the spots with a low gradient are created by intersection of blood vessels or connecting tissues. On the other hand, spots with very steep slopes are created mainly by artifacts (damages in the emulsion). To estimate the gradient, one uses the border or perimeter of the spot corresponding to the local maximum, i.e., the "upper border", and the border or perimeter of the spot, which represents the slope, i.e., the "bottom border". Because the difference in brightness between the upper and lower borders is known [(Fmax−Fmin)/N], the distance between these borders (in number of pixels, for example) is proportional to the value of the gradient at the slope. Thus, determination of the gradient can be done at a very low computational cost because the binary bitmaps that were already prepared at the previous step for finding bright spots (local maximums) are used, and the only additional requirement is that the number of pixels between the borders be counted. It should be noted that since the spots are often asymmetric and irregular in shape (particularly those associated with a malignancy), this distance may be different in different directions. Therefore, the slope may have different gradients on different directions.

Another aspect of calcification detection subsystem 1202 is to classify the spots as calcifications or non-calcifications. For this purpose, several characteristics of the spot are calculated including, but not limited to: 1) the area of the top spot, 2) the area of the bottom spot, 3) the length of the top border, 4) the length of the bottom border, 5) the area-to-border ratio for the top spot, 6) the area-to-border ratio for the bottom spot. To separate the calcifications from other bright spots, a pattern recognition technique based on SVM machines is used.

In most problems of image interpretation, the context of each part of an image must be taken into consideration. This is true for the problem of identifying calcifications in mammograms as well. At least three characteristics of the surrounding area of a given bright spot at level L should be considered: 1) the total area of spots at the level L−1 inside a circle of radius RI around the top spot, 2) the proximity of other objects with more prominent characteristics of calcification, and 3) whether the spot is located on a blood vessel. (Vascular calcifications can be seen as parallel tracks or linear tubular calcifications that run along a blood vessel and are typically classified as benign.) Asia result of such non-local approach, the following procedure of finding calcifications is used:

A. Find a bright spot.
B. Calculate the geometrical characteristics.
C. Use the SVM to recognize the prominent calcifications.
D. Soften the restrictions for calcification recognition and apply these criteria in the vicinity of the prominent calcifications.
E. Determine whether the "calcification" is located on a vessel and, if so, delete it.

The following provides a method for identifying blood vessels in step E. For this purpose, each spot at each binary bitmap is analyzed as follows:

$E_1$ Find the border pixels.
$E_2$ Keep the kernel pixels which are common to opposite borders (left and right borders or top and bottom borders).
$E_3$ Delete the kernel pixels belonging to the upper border.
$E_4$ Find the border pixels.
$E_5$ Delete the border pixels belonging to the right border.
$E_6$ Find the border pixels.
$E_7$ Delete the border pixels belonging to the bottom border.
$E_8$ Find the border pixels.
$E_9$ Delete the border pixels belonging to the left border.
$E_{10}$ Return to point $E_1$ and repeat all steps until all pixels on the bitmap are kernel pixels.

Figure 13:
FIG. 13 is a bit mapped image following feature extraction processing of calcification images containing in a mammogram.

The preceding sequence of steps $E_1$-$E_{10}$ for identification of vessels will transform each spot that is generally shaped as a strip, i.e., elongated as a vessel would be, into what looks like a central line (a set of connected pixels), or a "skeleton" of the strip, as shown in the upper image of FIG. 13. For spots that are not shaped as a strip, i.e., not a vessel, the set of kernel pixels determined according to steps $E_1$-$E_{10}$ will not create a connected line of appropriate length, thus indicating that the spot is not a vessel. See, e.g., the lower image of FIG. 13.

Clusters of micro-calcifications are characterized by their relatively small sizes and high densities. The algorithm combines a recursive peak seeking technique with morphological operations to achieve a highly accurate calcification detection and segmentation.

Segmentation to distinguish overlapping or closely positioned objects according to the preferred embodiment is described above with reference to FIG. 5, and therefore will not be repeated. Briefly, however, where overlapping calcifications are identified, a gravitation model is applied to contract the objects to allow them to be distinguished.

Following Calcification Segmentation (step 1212), Local SVM analyzer 1222 analyzes the characteristics of individual calcifications detected by the segmentation algorithm. A quantitative measure of the likelihood of a calcification being associated with malignancy is produced by the SVM. All the evaluations from the first stage local SVM analyzer 1222 are used by the second stage global SVM 1242 for a more global assessment of the cluster.

Figure 14:
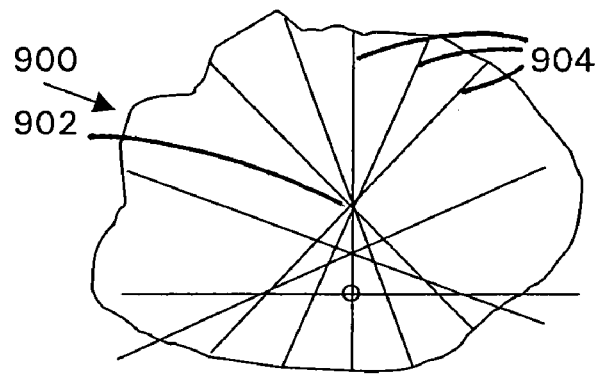
FIG. 14 is a diagram illustrating a pre-processing transformation for converting image segments to fixed dimensional form.

For a given SVM, the input data must have the same dimension. Because segmented calcifications will vary in sizes, proper transformations are necessary to convert the variable size image segments to a fixed dimensional form without losing critical information. The following transformation sequence converts the contour of a calcification to a fixed dimensional vector and is illustrated in FIG. 14.

1. Compute the centroid 902 of the calcification 900.
2. Use the centroid 902 as the origin of a polar coordinate system and sample the contour of the calcification with n equally spaced angles. This gives n radial measures 904 which form an n dimensional vector $[r_1, r_2, K, r_n]$.
3. Apply a discrete Fourier transform to the vector obtained in step 2. The resulting n-dimensional complex vector is used as the input to the SVM.

Because n is the predetermined number of sampling radial rays, the dimension of the resulting vector is fixed regardless of input calcification size. This approach avoids the unnatural re-sampling or padding. The Fourier transform takes advantage of the periodic nature of the sampling scheme and further enhances the essential features such as the rotational invariants.

Referring again to FIG. 11, the result of the Local SVM analysis step 1222 is then processed for feature extraction (step 1232). Features known to be relevant in discriminating malignant and benign calcifications are extracted and the results are fed to the Global SVM classifier 1242. Useful features include the number of calcifications, areas, perimeters, locations, orientations, and eccentricities of the calcifications.

Due to the ability of SVMs to process high dimensional input data without sacrificing generalization, a large number of features can be added to the input. Even though the contribution of an individual feature to the classifier may be small, the entire set of features can collectively provide the SVM with sufficient information to achieve proper classification.

An important component in any SVM or other kernel-based method is the kernel used to define the inner product in the feature space. The kernel describes the similarities between the input vectors in a non-linear fashion. The performance of a kernel-based system is largely dependent upon the proper design of the kernel that captures the essential features of the given problem. In the preferred embodiment, a Fourier kernel is used to specifically address the problem of geometric shape recognition and classification. It is clearly desirable that the kernel be invariant under the transformations of translations and rotation. The detected contour from an image will also vary in size. The kernel needs to be robust enough to accommodate a large range of shape patterns while still being sensitive enough to maintain critical information for classification. Given a contour, the Fourier kernel is computed as follows.

1. Given a contour that is a Jordan (simple continuous closed) curve in the plane, represent the contour as a complex-valued function z(s), $0 \leq s \leq 1$. Regard the origin of the complex plane at the centroid of the contour and associate the points on the contour with the complex numbers of the function.
2. Compute the Fourier coefficients of z(s) up to order N.

$$f_n = \int_0^1 z(s)e^{-2\pi i n s} ds, -N \leq n \leq N \qquad (1)$$

3. For two contours z(s), w(s) with Fourier coefficients $f_n$, $g_n$, the kernel is defined as $$K(z, w) = \sum_{n=-N}^{N} |f_n \cdot g_n| \qquad (2)$$

The Fourier kernel has many advantages over other kernels in dealing with the shape classification problem in that: 1) the Fourier kernel is translation and rotation invariant. A translated or rotated shape will be considered exactly the same as the original one by the kernel. The invariance is accomplished completely automatically and transparently in the design of the kernel. It does not require any costly alignments or searches. 2) The Fourier kernel is faithful in retaining critical information for shape classification. The Fourier series is an exact representation of the original contour. With a finite number of terms, it is still an accurate approximation to the original. The rotational feature is filtered out in a natural way without affecting other essential features. 3) The Fourier kernel is computationally efficient. A small number of terms (e.g. N=10) is usually sufficient for most practical applications. It can also take advantage of existing fast algorithms such as Fast Fourier Transform (FFT) to achieve greater efficiency.

Other types of transforms which are well known in the art can be used to facilitate extraction of useful data from the original image data rather than analyzing the image data directly. One such transform, the "wavelet transform", provides a powerful tool for multiresolution analysis of the images. Wavelet transforms localize a function both in space and scaling. The coefficients in the wavelet transforms can be used as features at certain scales for the SVM classifier.

Another type of transform, the "Radon transform", maps image points in the space domain to a sinusoidal curve in the Radon transform domain to provide parameters of all possible curves on which the point may lie. An important property of the Radon transform is to extract lines (curves) from very noisy images. Two-dimensional Radon transforms can generate numerical descriptions of many useful features related to the shapes of objects, including convexity, elongation, angularity, and the number of lobes. (For a discussion of use of the two dimensional Radon transform for analysis of shape, see Leavers, V. F., "Use of the Two-Dimensional Radon Transform to Generate a Taxonomy of Shape for the Characterization of Abrasive Powder Particles", IEEE *Transactions on Pattern Analysis and Machine Intelligence*, Vol. 22, No.23, December 2000 which is incorporated herein by reference.) The Hough transform, a special case of the Radon transform, is a standard tool in image analysis that allows recognition of global patterns in an image space by recognition of local patterns (ideally a point) in a transformed parameter space. It is particularly useful when the patterns sought are sparsely digitized, have holes and/or the images are noisy. (The Radon function available in the Image Processing Toolbox of commercially-available MatLab® software (The MathWorks, Inc., Natick, Mass.) can also be used to implement the Hough transform.) The SVM within Global SVM classifier 1242 is trained to classify the malignant and benign calcifications based on the selected features and the results of the local SVM analyzer 1222. A training data set of an approximately equal number of benign and cancer calcification cases are used to train the Global SVM analyzer 1242. The resulting SVM is tested on an independent test data set to evaluate its performance and generalization capability. The training process is iterated to select the optimal kernels and structures for the SVM. Using a multiple SVM configuration such as the example shown in FIG. 9, multiple SVMs may be provided to process the same training and test data sets, then selecting the SVM that provides the optimal output to process live data.

An enhanced version of a soft margin SVM is used in the preferred embodiment of the Global SVM classifier 1242. A traditional soft margin SVM is constructed by maximizing the functional $$W(\alpha) = \sum_{i=1}^{l} \alpha_i - \frac{1}{2} \sum_{i,j}^{l} \alpha_i \alpha_j y_i y_j K(x_i, x_j) \quad (3)$$

subject to the constraints $$\sum_{i=1}^{l} \alpha_i y_i = 0 \quad (4)$$

$$0 \leq \alpha_i \leq C, \quad i = 1, 2, K, l$$

The constant C is selected to penalize the misclassified points.

In the enhanced soft margin SVM, the constant C is not necessarily the same for all input vectors. In particular, one may choose different Cs for benign cases and malignant cases to associate different penalties with missed cancers and false alarms. The enhanced SVM is constructed by maximizing the functional $$W(\alpha) = \sum_{i=1}^{l} \alpha_i - \frac{1}{2} \sum_{i,j}^{l} \alpha_i \alpha_j y_i y_j K(x_i, x_j) \quad (5)$$

subject to the constraints $$\sum_{i=1}^{l} \alpha_i y_i = 0 \quad (6)$$

$$0 \leq \alpha_i \leq C_i, \quad i = 1, 2, K, l$$

Mass detection subsystem 1204 is similar to the calcification subsystem 1202. However, instead of calcification, the preprocessing steps of the subsystem 1204 are specifically designed to detect and segment masses and to extract features associated with the masses. The SVM training procedures are the same as the calcification subsystem 1202.

An important indicator of abnormalities is the asymmetric density patterns between the left and right images and the changes in mammogram images taken at different times. Detecting asymmetric dense regions can significantly improve the performance of the entire system. Clearly, it is not realistic to expect a perfect match even for symmetrical cases, therefore, the matching and registration algorithm used for asymmetry detection (step 1214) will allow normal small variations in the density patterns. The main focus of the algorithm will be the topological differences of the relatively high density areas between the two images. The procedure for asymmetry detection 1214 is as follows:

1. Construct two graphs representing the dense areas in the two images under comparison.
2. Find an optimal matching between the vertices of two graphs.
3. Evaluate the mismatched vertices and eliminate the ones that can be merged into adjacent vertices within acceptable variations.
4. The remaining mismatched vertices represent the asymmetric densities.

The appearances of masses in mammogram images are usually much more subtle than the calcifications. In mass segmentation step 1224, geometric transformation techniques are used to detect the often ill-defined boundaries. Hough transforms, described above, can be applied to detect specific shapes such as lines or circles in the images. Radon transforms are useful in handling irregular shapes.

Feature extraction step 1234 is performed in the same manner as the feature extraction step 1232 of calcification subsystem 1202. Important features to be extracted are location, size, shape, margins and x-ray attenuation. Evaluation of additional qualities, such as textures of the mass area, may also be useful for feature extraction in the mass detection subsystem 1204.

SVM classifier 1244 is trained and tested using a procedure similar to that used for Global SVM classifier 1242 in the calcification subsystem. SVM classifier 1244, comprising one or more SVMs, receives the output of feature extraction step 1234 and classifies the data into appropriate categories for each of the extracted features. For example, mass shape may have one of the following characteristics: round, oval, lobular or irregular, such that that SVM classifier 1244 would distribute the data into one of the four categories of shape characteristic. Similarly, there are five types of margins: circumscribed, obscured, micro-lobulated, ill-defined and spiculated, and SVM classifier would divide the data into one of the five margin categories. In view of the number of different mass-related features that are relevant to diagnosis of malignancy, it may be desirable to structure SVM classifier 1244 into a hierarchical configuration, assigning at least one first-level SVM to each feature, then combining the optimal outputs for processing through higher level SVMs until a single output is generated from SVM classifier 1244. This output is input to global SVM analyzer 1250 which combines the mass detection results with the results of the calcification and structure distortion subsystems to produce a diagnosis.

Structural distortion detection subsystem 1206 is similar to the calcification subsystem 1202. The preprocessing steps, spiculation detector 1216 and feature extraction 1226, are specifically designed to detect suspicious regions and extract features associated with structure distortions. Spiculations, which typically appear as radiating lines, or a "sunburst" pattern, can represent a desmoplastic process in conjunction with a possibly infiltrating tumor. On the other hand, postsurgical scarring from a previous biopsy, radial scars, trauma, and infection may also produce a lesion with spiculated margins. The presence of spiculations in conjunction with the results of the other detection subsystems thus provide a good diagnostic tool. The SVM training procedures for SVM classifier 1236 are the same as for the classifiers previously described for the other detection subsystems. The output of SVM classifier 1236 will typically provide an output indicating the presence or not of spiculated distortions. This output is combined with the outputs of the other detection subsystems for input to overall SVM analyzer 1250 for use in the diagnosis of presence or not of a malignancy.

While the preceding example describes a procedure for analysis of mammograms for diagnosis of breast cancer, applications of computer-aided image analysis according to the present invention are not so limited, but are as wide-ranging as the applications of digital imaging itself. Generally, any situation in which a digital image is to be analyzed to aid in decision making, e.g., medical, industrial, geologic and space exploration, air or satellite reconnaissance, etc., or simply to provide information about the subject matter of the image where the image contains many data points that are subject to a number of interpretations, can benefit by employing image analysis according to present invention.

Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A method for automated analysis of a digitized microscope image of a medical specimen having a plurality of features of interest, the method comprising:
   storing a plurality of detection subsystems in a memory device in communication with a processor, wherein each of the plurality of detection subsystems comprises a pre-processing component for detecting and extracting one of the features of interest within the microscope image, a classification component comprising at least one first-level support vector machine for classifying the extracted feature of interest into at least one of a plurality of possible feature classes, an output for outputting the classified feature of interest, and an overall analyzer for combining the outputs of the plurality of detection subsystems and generating an analysis of the microscope image, the overall analyzer comprising a second-level support vector machine;
   receiving digitized microscope image data to be processed in the processor; and
   processing the digitized microscope image data to classify the features of interest and generate an output comprising an analysis of the digitized microscope image.

2. The method of claim 1, wherein the medical specimen is a cytology specimen.

3. The method of claim 1, wherein the medical specimen is a tissue sample.

4. The method of claim 1, wherein the microscope image comprises a plurality of a single type of feature of interest and the pre-processing component comprises a segmentation function for separating overlapping features of interest in the microscope image.

5. The method of claim 4, wherein the segmentation function comprises a gravitation model that is applied to each overlapping feature of interest to contract each feature into a distinct body.

6. The method of claim 1, wherein the pre-processing component comprises a segmentation function for separating the feature of interest from a background and generating a numerical value for the segmented feature of interest.

7. The method of claim 6, wherein segmenting comprises identifying local extremes corresponding to each segmented feature of interest in the image data.

8. The method of claim 7, wherein the feature of interest comprises a spot having a brightness and identifying local extremes comprises classifying the brightness of the spot into one or more of a plurality of brightness levels.

9. The method of claim 8, wherein geometry is a possible feature characteristic and geometry is determined measuring a change in slope between borders of the spot at two different brightness levels.

10. The method of claim 1, wherein the pre-processing component comprises a segmentation function for segmenting the feature of interest and transforming the segmented feature to a fixed dimensional vector.

11. The method of claim 10, wherein transforming comprises:
    computing a centroid of the feature of interest;
    sampling a contour of the feature of interest using a polar coordinate system having an origin at the centroid to provide a plurality of radial measures;
    forming a vector using the plurality of radial measures; and
    applying a Fourier transform to the vector to provide the fixed dimensional vector.

12. A computer system for analysis of a digitized microscope image of a medical specimen having a plurality of features of interest, the computer system comprising:
    a processor programmed for executing a plurality of support vector machines;
    an input device for receiving image data to be processed;
    a memory device in communication with the processor having a plurality of detection subsystems stored therein for execution by the processor, each of the plurality of detection subsystems comprising:
       a pre-processing component for detecting and extracting one of the features of interest within the image data;
       a classification component comprising at least one first-level support vector machine for classifying the feature of interest into at least one of a plurality of possible features characteristics;
       an output for outputting the classified feature of interest;
    an overall analyzer for combining the outputs of the plurality of detection subsystems and generating an analysis of the digitized microscope image, the overall analyzer comprising a second-level support vector machine.

13. The computer system of claim 12, wherein pre-processing component applies a segmenting routine to separate the feature of interest from a background and generates a numerical value for the segmented feature of interest.

14. The computer system of claim 13, wherein segmenting routine identifies local extremes corresponding to each segmented feature of interest in the image data.

15. The computer system of claim 14, wherein the feature of interest comprises a spot having a brightness and local extremes are identified by classifying the brightness of the spot into one or more of a plurality of brightness levels.

16. The computer system of claim 15, wherein geometry is a possible feature characteristic and geometry is determined by measuring a change in slope between borders of the spot at two different brightness levels.

17. The computer system of claim 12, wherein the pre-processing component segments the feature of interest and applies a transform to the segmented feature to a fixed dimensional vector.

18. The computer system of claim 17, wherein transform comprises:
   computing a centroid of the feature of interest;
   sampling a contour of the feature of interest using a polar coordinate system having an origin at the centroid to provide a plurality of radial measures;
   forming a vector using the plurality of radial measures; and
   applying a Fourier transform to the vector to provide the fixed dimensional vector.

19. The computer system of claim 12, wherein each digitized image includes a plurality of a single type of feature of interest and the pre-processing component segments a first feature of interest from a second, at least partially overlapping feature of interest by applying a gravitation model to each feature of interest to contract each feature into a distinct body.

20. The method of claim 12, wherein the medical specimen is a cytology specimen.

* * * * *